(12) United States Patent
Petasis et al.

(10) Patent No.: US 7,247,701 B2
(45) Date of Patent: Jul. 24, 2007

(54) AMINO AMIDES, PEPTIDES AND PEPTIDOMIMETICS

(75) Inventors: Nicos A. Petasis, Hacienda Heights, CA (US); Xin Yao, Guilderland, NY (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 11/227,986

(22) Filed: Sep. 14, 2005

(65) Prior Publication Data

US 2006/0063206 A1 Mar. 23, 2006

Related U.S. Application Data

(62) Division of application No. 10/405,927, filed on Apr. 1, 2003, now Pat. No. 6,946,542.

(60) Provisional application No. 60/369,542, filed on Apr. 1, 2002.

(51) Int. Cl.
*A61K 38/00* (2006.01)

(52) U.S. Cl. .............. 530/300; 530/333; 530/334; 530/335; 530/336; 530/337

(58) Field of Classification Search .............. None
See application file for complete search history.

(56) References Cited

U.S. PATENT DOCUMENTS

| | | | |
|---|---|---|---|
| 4,442,099 A | 4/1984 | Nicolaou et al. | 424/248.57 |
| 4,567,290 A | 1/1986 | Nicolaou et al. | 560/124 |
| 4,710,521 A | 12/1987 | Soukup et al. | 521/118 |
| 4,759,880 A | 7/1988 | Nicolaou et al. | 260/413 |
| 5,087,790 A | 2/1992 | Petasis et al. | 585/638 |
| 5,136,501 A | 8/1992 | Silverman et al. | 364/408 |
| 5,177,046 A | 1/1993 | Savoca et al. | 502/167 |
| 5,594,732 A | 1/1997 | Bell et al. | 370/401 |
| 5,596,123 A * | 1/1997 | Elgendy et al. | 558/288 |
| 5,752,238 A | 5/1998 | Dedrick | 705/14 |
| 5,756,789 A | 5/1998 | Bruce et al. | 556/14 |
| 5,842,040 A | 11/1998 | Hughes et al. | 395/831 |
| 5,845,265 A | 12/1998 | Woolston | 705/37 |
| 5,870,717 A | 2/1999 | Wiecha | 705/26 |
| 5,878,400 A | 3/1999 | Carter, III | 705/20 |
| 5,878,423 A | 3/1999 | Anderson et al. | 707/100 |
| 5,890,138 A | 3/1999 | Godin et al. | 705/26 |
| 5,896,379 A | 4/1999 | Haber | 370/390 |
| 5,946,467 A | 8/1999 | Pathakis et al. | 395/200.66 |
| 6,030,715 A | 2/2000 | Thompson et al. | 428/690 |
| 6,030,917 A | 2/2000 | Weinberg et al. | 502/104 |
| 6,069,109 A | 5/2000 | Kao et al. | 502/152 |
| 6,232,467 B1 * | 5/2001 | Petasis et al. | 544/171 |
| 6,259,699 B1 | 7/2001 | Opalka et al. | 370/398 |
| 6,272,474 B1 | 8/2001 | Garcia | 705/37 |
| 6,336,105 B1 | 1/2002 | Conklin et al. | 705/80 |
| 6,336,138 B1 | 1/2002 | Caswell et al. | 709/223 |
| 6,377,937 B1 | 4/2002 | Paskowitz | 705/26 |
| 6,397,212 B1 | 5/2002 | Biffar | 707/5 |
| 6,415,270 B1 | 7/2002 | Rackson et al. | 705/37 |
| 6,427,132 B1 | 7/2002 | Bowman-Amuah | 703/22 |
| 6,602,817 B1 | 8/2003 | Petasis | 502/172 |
| 2003/0236423 A1 | 12/2003 | Petasis | 554/61 |

FOREIGN PATENT DOCUMENTS

| | | |
|---|---|---|
| EP | 0 736 509 A2 | 10/1996 |
| EP | 0 736 509 B1 | 11/2001 |
| WO | WO 97/19415 | 5/1997 |
| WO | WO 98/19259 | 5/1998 |
| WO | WO 98/35469 | 8/1998 |
| WO | WO 99/06913 | 2/1999 |
| WO | WO 99/13417 | 3/1999 |

OTHER PUBLICATIONS

Babine, R. E. and S.L. Bender., "Molecular Recognition of Protein-Ligand Complexes: Applications to Drug Design," *Chem. Rev.* 97:1359-1472 (1997).
Bhaley, G. et al., "Solid-Phase Synthesis of Diverse Tetrahydro-1,4-Benzodiazepine-2-ones," *Tetrahedron Letters* 38(48):8375-8378 (1997).
Bläser, E. et al., "Asymmetric Steering of Oxa Diels—Alder Reactions with Silyloxydienes Employing Proline Esters as Chiral Auxiliary Groups," *Eur. J. Org. Chem.*, 329-333, (1999).
Deloux, Laurent and Morris Srebnik "Asymmetric Boron-Catalyzed Reactions", *Chem. Rev.* 93:763-784, (1993).
Durantel. et al., "Study of the Mechanism of Antiviral Action of Iminosugar Derivatives against Bovine Viral Diarrhea Virus," *J. Virology* 75(19): 8987-8998, (2001).
Du Bois, et al., "Novel, Stereoselective Synthesis of 2-Amino Saccharides," *J. Am. Chem. Soc.* 119:3179-3180, 1997.
Evans, B.E. et al., "Design of Nonpeptidal Ligands for a Peptide Receptor: Cholecystokinin Antagonists," *J. Med. Chem.* 30:1229-1239 (1987).
Fletcher, M. D. and M.C. Campbell, "Partially Modified Retro-Inverso Peptides: Development, Synthesis, and Conformational Behavior," *Chem. Rev.*, 98:763-795, (1998).
Garro-Helion, et al., "Mild and Selective Palladium(0)-Catalyzed Deallylation of Allylic Amines. Allylamine and Diallylamine as Very Convenient Ammonia Equivalents for the Synthesis of Primary Amines," *J. Org. Chem.*, 58:6109-6113, (1993).
Golebiowski, A. and J. Jurczak, "α-Amino-β-hydroxy Acids in the Total Synthesis of Amino Sugars," *Synlett*, pp. 241-245, (Apr. 1993).
Guillier et al., "Linkers and Cleavage Strategies in Solid-Phase Organic Syntheis and Combinatorial Chemistry,"*Chem. Rev.*, 100:2091-2157, (2000).

(Continued)

*Primary Examiner*—B. Dell Chism
(74) *Attorney, Agent, or Firm*—Fish & Richardson P.C.

(57) ABSTRACT

Synthetic methods and compounds involving amino amides, peptides and peptidomimetics. Amino amide derivatives are prepared via the one-step three-component reaction of a glyoxamide, an amine, and an organoboron derivative. Conversion of the product to another glyoxamide intermediate allows the iterative use of this chemistry for the synthesis of peptides and peptidomimetics.

11 Claims, No Drawings

OTHER PUBLICATIONS

Hanessian, S. et al., "Design and Synthesis of Conformationally Constrained Amino Acids as Versatile Scaffolds and Peptide Manners," *Tetrahedron*, 53:12789-12854, (1997).

Hoyng, C.F. and A.D. Patel, Aldehyde Components for Use in Four-Component Condensation ("4CC") UGI Reaction Peptide Synthesis, *Tetrahedron Lett.*, 21:4795-4798, (1980).

Humphrey, J.M. and A.R. Chamberlin, Chemical Synthesis of Natural Product Peptides: Coupling Methods for the Incorporation of Noncoded Amino Acids into Peptides, *Chem. Rev.*, 97:2243-2266, (1997).

Kö nig et al., "Synthesis of N-tert-Alkylglyoxylic Acid Amides," *Synthesis*, pp. 1233-1234, (1993) [in German, English language abstract on 1st page of article].

Marx et al., "Synthetic Design for Combinatorial Chemistry. Solution and Polymer-Supported Synthesis of Polycyclic Lactams by Intramolecular Cyclization of Azomethine Ylides," *J. Am. Chem. Soc.*, 119:6153-6167, (1997).

Mehta et al., "Structure-Activity Relationship of a New Class of Anti-Hepatitis B Virus Agents," *Antimicrobial Agents and Chemotherapy*, 46(12):4004-4008 (2002).

Nicolaou et al., "Novel IBX-Mediated Process for the Synthesis of Amino Sugars and Libraries Thereof," *Angew. Chem. Int. Ed. Engl.*, 39:2525-2529, (2000).

Nicolaou, et al., "Lipoxins and Related Eicosanoids: Biosynthesis, Biological Properties, and Chemical Synthesis," *Angew. Chem. Int. Ed. Engl.* 30:1100-1116, (1991).

Noyori, R. (Ed.), "Enantioselective Addition of Organometallic Reagents to Carbonyl Compounds: Chirality Transfer, Multiplication, and Amplification, " Chapter 5 in *Asymmetrical Catalysis in Organic Synthesis*, New York: John Wiley & Sons, Inc., pp. 255-297 (1994).

Nugent, William A., "Chiral Lewis Acid Catalysis. Enantioselective Addition of Azide to Meso Epoxides",*J. Am. Chem. Soc.*, 114(7): 2768-2769 (1992).

O'Donnell, Martin J. and J. Falmagne, "The Synthesis of Amino Acids via Organoboranes." *J. Chem. Soc. Chem. Commun.*, No. 17, pp. 1168-1169, (Sep. 1, 1985).

Petasis, N. A. and I.A. Zavialov, "The Boronic Acid Mannich Reaction: A New Method for the Synthesis of Geometrically Pure Allylamines." Tetrahedron Letters, 34(4):583-586, (1993).

Petasis, N.A. and I.A. Zavialov, "A New and Practical Synthesis of α-Amino Acids from Alkenyl Boronic Acids," *J. Am. Chem. Soc.*, 119(2):445-446, (1997).

"Scope and Editorial Policy," *Organometallics*, published by the American Chemical Society 21(1):13A, 14A (2002).

Serhan et al., Novel Functional Sets of Lipid-derived Mediators with Antiinflammatory Actions Generated from Omega-3 Fatty Acids via Cyclooxygenase 2-Nonsteroidal Antiinfammatory Drugs and Transcellular Processing, *J. Exp. Med*. 192:1197-1204, (2000).

Thompson, L.A. and J.A. Ellman, "Synthesis and Applications of Small Molecule Libraries," *Chem. Rev.* 96:555-600 (1996).

Waki, M. and J. Meienhofer, "Peptide Synthesis Using the Four-Component Condensation (Ugi Reaction)," *J. Am. Chem. Soc.*, 99:6075-6082, (1977).

Yamamoto, Y. and N. Asao, "Selective Reactions Using Allylic Metals." *Chem. Rev.*, 93:2207-2293, (1993).

\* cited by examiner

AMINO AMIDES, PEPTIDES AND PEPTIDOMIMETICS

CROSS REFERENCE TO RELATED APPLICATIONS

This application is a divisional application of U.S. Ser. No. 10/405,927, filed Apr. 1, 2003, now U.S. Pat. No. 6,946,542, which claims the benefit of U.S. Provisional Application No. 60/369,542, filed on Apr. 1, 2002. The entire teachings of these applications are incorporated herein by reference.

STATEMENT REGARDING FEDERALLY SPONSORED RESEARCH

The U.S. Government may have certain rights in this invention pursuant to Grant No. GM45970 awarded by the National Institutes of Health.

BACKGROUND

The present application relates to amino amides, peptides and peptidomimetics, and methods for preparing such compounds.

The unique roles of various peptides, including their function as extra-cellular messengers, hormones, neurotransmitters neuromodulators, and immune defense modulators, is well established. Consequently, the use of peptides or amino amides containing natural and unnatural amino acid units against many therapeutic targets is of continued interest. Numerous methods have been developed for the synthesis of amino amides or peptides both in solution and on a solid support (Bodanszky, M. Principle of Peptide Synthesis, 2nd Edition, Springer-Verlag, Berlin, 1993; Guillier, F.; Orain, D.; Bradley, M. Chem. Rev., 100:2091; 100:2091; 2000; Humphrey, J. M.; Chamberlin, A. R. Chem. Rev., 97:2243, 1997).

Due to difficulties resulting from the limited selectivity, stability, delivery and bioavailability of certain peptides, the design and synthesis of peptidomimetic molecules continues to be at the forefront of drug design and discovery and many peptidomimetic frameworks and methods for their synthesis have been developed (Babine, R. E.; Bender, S. L., Chem. Rev., 97:1359, 1997; Hanessian, S.; et al., Tetrahedron, 53:12789, 1997; Fletcher, M. D.; Cambell, M. C., Chem. Rev., 98:763, 1998).

Traditional peptide synthesis in both solution phase and solid phase involves the stepwise or iterative use of the following six transformations: (a) synthesis of amino acid units; (b) monoprotection of certain amino acid units at their N-terminus; (c) monoprotection of certain amino acid units at their C-terminus; (d) coupling of an N-protected and a C-protected amino acid unit via amide bond formation; (e) removal of the protecting group from the N-terminus; and (f) removal of the protective group from the C-terminus. A number of unconventional approaches to the synthesis of peptides have also been developed, including the use of the Ugi four-component condensation reaction of acids, aldehydes, isocyanides and amines (Waki, M.; Meienhofer, J. J. Am. Chem. Soc., 99:6075, 1977; Hoyng, C. F.; Patel, A. D. Tetrahedron Lett., 21:4795, 1980).

Among the drawbacks of the traditional approaches to peptides and peptidomimetics is the large number of required reaction steps and the difficulties in incorporating certain unnatural amino acid side chains, such as alkenyl, alkynyl, allenyl, aryl and heteroaryl groups.

SUMMARY OF THE INVENTION

The present invention provides synthetic methods and compounds, involving amino amides, peptides and peptidomimetics. Amino amide derivatives are prepared via the one-step three-component reaction of a glyoxamide, an amine, and an organoboron derivative. Conversion of the product to another glyoxamide intermediate allows the iterative use of this chemistry for the synthesis of peptides and peptidomimetics.

In one aspect of the invention, which is outlined in Scheme 1, a peptide is prepared via the sequential use of the following three steps. Step A: conversion of an amine 1 to a glyoxamide 2; Step B: one-step three-component reaction between glyoxamide 2, an amine 3 and organoboron derivative 4 to form amino amide 5; and Step C: removal of at least one amine substituent from amino amide 5 to form amino amide 6. Iterative use of these three steps converts amino amide 6 to a dipeptide 11, while further iterations or conventional couplings with compounds 6 or 11 lead to oligopeptides or polypeptides.

Scheme 1

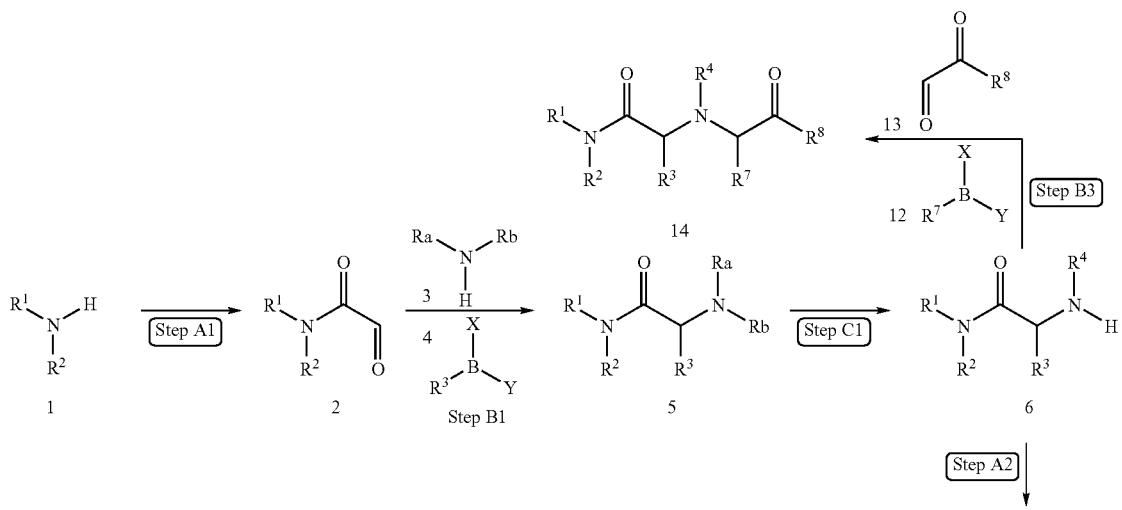

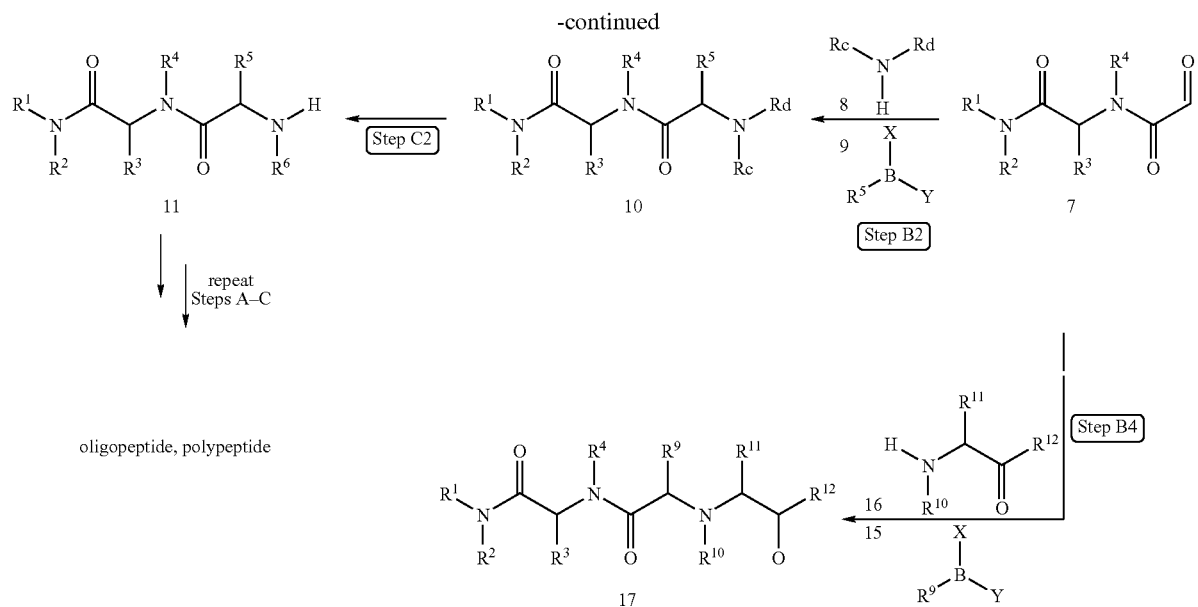

In another aspect, a conceptually related approach is used for the synthesis of peptidomimetics having one or more peptide bonds (N—C=O) replaced or switched by amine bonds. As outlined in Scheme 1, such peptidomimetics can be produced by using an amino amide intermediate (e.g., 6 or 11, or the starting amine derivative 1) as the amine component in the three-component process. For example, as shown in Scheme 1, reaction of amino amide 6 with and organoboron derivative 12 and glyoxamide 13 gives the peptidomimetic system 14. Alternatively, by using a glyoxamide intermediate (e.g., 2 or 7) as the carbonyl component in combination with an amino amide (or amino acid) as the amine component in the three-component process, a different type of peptidomimetic system is produced. For example, as shown in Scheme 1, reaction of 7 with amino amide 16 and organoboron derivative 15 gives the peptidomimetic derivative 17. This process can be used iteratively to attach additional amino acid units or it can be combined with a peptide-producing sequence to generate a large variety of peptidomimetic products.

The reactions of the present invention can be performed in solution or in the solid phase by incorporating one of the peptide or peptidomimetic substituents on a suitable solid support.

One step in the reactions of the present invention (Step A) involves the conversion of an amine, amino amide or peptide derivative to the corresponding glyoxamide. There are several known methods that can be used for the synthesis of glyoxamides (König, S.; Lohiberger, S.; Ugi, I. Synthesis, 1233, 1993; Marx, M. A. et al J. Am. Chem. Soc., 119:6153, 1997; Bläser, E. et al Eur. J. Org. Chem., 329, 1999), including the Swern oxidation of glycolamides, the ozonolysis of alkenylamides, and cleavage of diol amides. More substituted ketoamide derivatives can be generated similarly or using other known methods, and can be used in the place of glyoxamides, leading to even more substituted products.

Overall this approach does not require the pre-synthesis and mono-protection of the amino acid units, relying instead on the assembly of the amino acid moieties directly on the peptide or peptidomimetic framework. In this manner, a smaller number of overall steps is required, particularly if the peptide involves unnatural amino acid units.

In general, in one aspect, the present invention features a method of preparing an amino amide of formula 5 or formula 6. An amine derivative 1 is converted to a glyoxamide intermediate 2 which is reacted with an amine 3 and an organoboron derivative 4 to form amino amide 5. The use of a primary amine 3 having Ra=$R^4$ and Rb=H gives amino amide 6. Alternatively, compound 6 is produced from compound 5 via the removal of one or both substituents Ra and Rb, followed by the incorporation of $R^4$

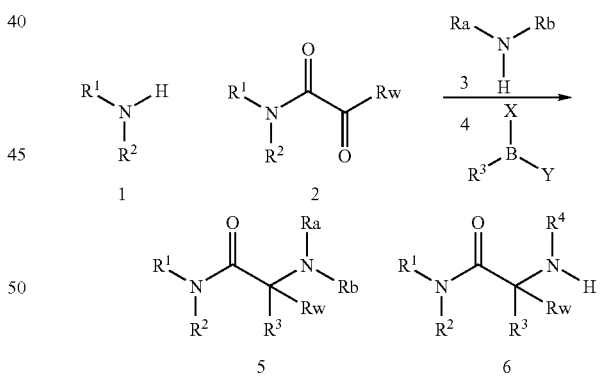

wherein:
$R^1$, $R^2$ and $R^4$ are independently selected from a group consisting of hydrogen, alkyl, allyl, alkenyl, aryl, heteroaryl, acyl, sulfonyl, amino, alkylamino, dialkylamino, acylamino, sulfonylamino, and alkoxy, provided that $R^1$ and $R^2$ can also be connected together forming a ring;
Rw can be hydrogen, alkyl, aryl or heteroaryl;
$R^3$ is alkyl, aryl, heteroaryl, allyl, alkenyl, alkynyl, or allenyl;
Ra and Rb are independently selected from a group consisting of hydrogen, alkyl, allyl, benzyl, aryl, heteroaryl, acyl, sulfonyl, amino, alkylamino, dialkylamino, acylamino, sulfonylamino, and alkoxy, provided that Ra and Rb can also be joined together forming a ring; and X and Y are independently selected from a group consisting of hydroxy, alkoxy, aryloxy, amino, alkylamino, and dialkylamino, provided that X and Y can also be joined together forming a ring.

In particular embodiments, $R^1$, $R^2$, $R^3$, Ra, Rb, Rw, X or Y can also be connected to a polymeric chain or other solid phase material.

In another aspect, the present invention features a method of preparing a peptide of formula 10 or of formula 11. An amino amide derivative 6 is converted to a glyoxamide intermediate 7 which is reacted with an amine 8 and an organoboron derivative 9 to form dipeptide 10. The use of a primary amine 8 having Rc=$R^6$ and Rd=H gives peptide 11. Alternatively, compound 11 is produced from compound 10 via the removal of one or both substituents Rc and Rd, followed by the incorporation of $R^6$

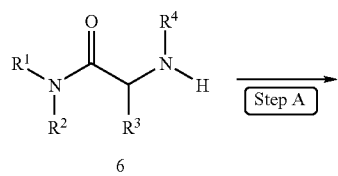

6

Step A

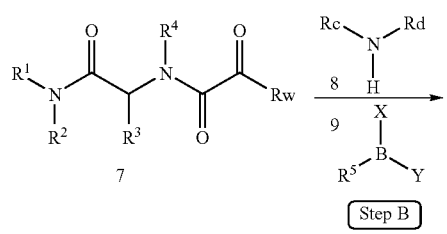

7

Step B

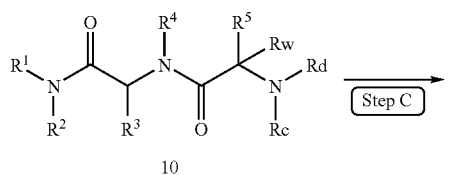

10

Step C

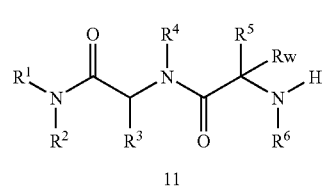

11 wherein:

$R^1$, $R^2$, $R^4$ and $R^6$ are independently selected from a group consisting of hydrogen, alkyl, allyl, alkenyl, aryl, heteroaryl, acyl, sulfonyl, amino, alkylamino, dialkylamino, acylamino, sulfonylamino, and alkoxy, provided that two or more of $R^1$, $R^2$, $R^4$ and $R^6$ can also be connected together forming one or more rings;

Rw is hydrogen, alkyl, aryl or heteroaryl.

$R^3$ and $R^5$ are independently selected from a group consisting of alkyl, aryl, heteroaryl, allyl, alkenyl, alkynyl, and allenyl;

Rc and Rd are independently selected from a group consisting of hydrogen, alkyl, allyl, benzyl, aryl, heteroaryl, acyl, sulfonyl, amino, alkylamino, dialkylamino, acylamino, sulfonylamino, and alkoxy, provided that Rc and Rd can also be joined together forming a ring; and X and Y are independently selected from a group consisting of hydroxy, alkoxy, aryloxy, amino, alkylamino, and dialkylamino, provided that X and Y can also be joined together forming a ring.

In particular embodiments, $R^1$, $R^2$, $R^3$, $R^4$, $R^5$, Rc, Rd, X or Y can be connected to a polymeric chain or other solid phase material.

In general, in another aspect, the present invention features a method of preparing a peptidomimetic of formula 14. An amino amide derivative 6 is reacted with a 1,2-dicarbonyl compound 13 and an organoboron derivative 12 to form peptidomimetic 14

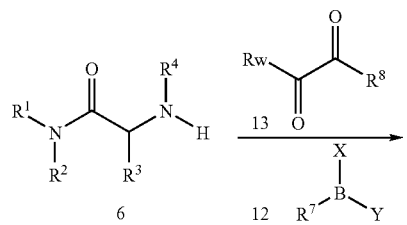

6      12

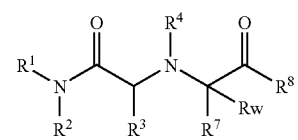

14 wherein:

$R^1$, $R^2$, and $R^4$ are independently selected from a group consisting of hydrogen, alkyl, allyl, alkenyl, aryl, heteroaryl, acyl, sulfonyl, amino, alkylamino, dialkylamino, acylamino, sulfonylamino, and alkoxy, provided that two or more of $R^1$, $R^2$, $R^3$ and $R^4$ can also be connected together forming one or more rings;

Rw is hydrogen, alkyl, aryl or heteroaryl.

$R^8$ is hydrogen, alkyl, alkenyl, aryl, heteroaryl, amino, alkylamino, dialkylamino, hydroxyamino, alkoxyamino, hydroxyl, alkoxy, aryloxy or heteroaryloxy;

$R^3$ and $R^7$ are independently selected from a group consisting of alkyl, aryl, heteroaryl, allyl, alkenyl, alkynyl, and allenyl; and X and Y are independently selected from a group consisting of hydroxy, alkoxy, aryloxy, amino, alkylamino, and dialkylamino, provided that X and Y can also be joined together forming a ring.

In particular embodiments, $R^1$, $R^2$, $R^3$, $R^4$, $R^7$, $R^8$, X or Y can also be connected to a polymeric chain or other solid phase material.

In general, in another aspect, the present invention features a method of preparing a peptidomimetic of formula 17. An amino amide derivative 6 is converted to a glyoxamide intermediate 7, which is reacted with and a organoboron derivative 15 and an amino carbonyl derivative 16 to form peptidomimetic 17

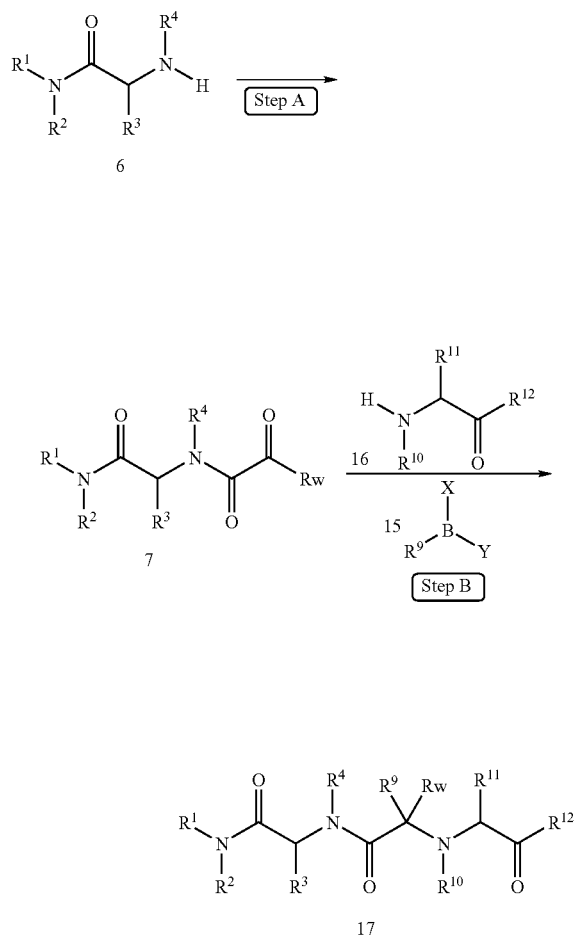

wherein:

$R^1$, $R^2$, $R^4$, and $R^{10}$ are independently selected from a group consisting of hydrogen, alkyl, allyl, alkenyl, aryl, heteroaryl, acyl, sulfonyl, amino, alkylamino, dialkylamino, acylamino, sulfonylamino, and alkoxy, provided that two or more of $R^1$, $R^2$, $R^3$ and $R^4$ can also be connected together forming one or more rings, and that two or more of $R^{10}$, $R^{11}$ and $R^{12}$ can also be connected together forming one or more rings;

Rw is hydrogen, alkyl, aryl or heteroaryl.

$R^3$, $R^9$ and $R^{11}$ are independently selected from a group consisting of alkyl, aryl, heteroaryl, allyl, alkenyl, alkynyl, and allenyl;

$R^{12}$ is hydrogen, alkyl, alkenyl, aryl, heteroaryl, amino, alkylamino, dialkylamino, hydroxyamino, alkoxyamino, hydroxyl, alkoxy, aryloxy or heteroaryloxy; and X and Y are independently selected from a group consisting of hydroxy, alkoxy, aryloxy, amino, alkylamino, or dialkylamino, provided that X and Y can also be joined together forming a ring.

In particular embodiments, $R^1$, $R^2$, $R^3$, $R^4$, $R^9$, $R^{10}$, $R^{11}$, $R^{12}$, Rw, X or Y can also be connected to a polymeric chain or other solid phase material.

Particular embodiments of the invention can provide one or more of the following advantages. The synthetic methods of the invention provide an efficient and practical route to novel structures that are not readily available by other methods. The methods are highly versatile, allowing a high degree of structural variation in the reacting components. The methods allow the formation of complex amino amides peptides and peptidomimetics from several readily available building blocks. For these reasons, the methods are readily applicable to solid or liquid phase combinatorial synthesis.

The reactions with the organoboron derivatives can be carried out in water or aqueous solvents at ambient temperature, allowing the synthesis of highly hydrophilic products without the need for unnecessary protection-deprotection steps. The reactions can be carried out without using toxic, hazardous or corrosive materials, such as cyanides, strong acids, strong bases, organotin, organocopper or other highly reactive organometallic compounds. The reactions do not require an inert atmosphere, and can be done in the air. In particular, the organoboronic acids used in some embodiments are often crystalline, easy to prepare and easy to handle compounds that are stable in air and water. They are also non toxic and non hazardous.

By using the synthetic methods of the present invention, the amino amides, peptides and peptidomimetics can be prepared using a smaller number of synthetic steps than most existing methods. Starting materials used in the reactions are generally either commercially available or can be readily prepared from commercially available reagents by a procedure involving one or more steps.

The stereochemical control of the reactions can be accomplished not only with the use of chiral amine and carbonyl components but also with chiral organoboron derivatives. Boron-based auxiliaries can be easily introduced and can be efficiently recycled after the reaction, thus making this method especially attractive for large scale applications. Due to the facile synthesis of alkenyl and aryl boron derivatives, which proceed with complete control of geometry or positional isomerism, isomerically pure products can be obtained.

The details of one or more embodiments of the invention are set forth in the description below. Unless otherwise defined, all technical and scientific terms used herein have the meaning commonly understood by one of ordinary skill in the art to which this invention belongs. All publications, patent applications, patents, and other references mentioned herein are incorporated by reference in their entirety. In case of conflict, the present specification, including definitions, will control. Other features and advantages of the invention will become apparent from the description and the claims.

DETAILED DESCRIPTION

Definitions:

An organoboron derivative, as defined herein, comprises a compound having a boron atom connected to at least one alkyl, allyl, alkenyl, aryl, allenyl or alkynyl group.

As used in this specification, alkyl groups can include straight-chained, branched and cyclic alkyl radicals containing up to about 20 carbons. Suitable alkyl groups may be saturated or unsaturated. Further, an alkyl may also be substituted one or more times on one or more carbons with substituents selected from the group consisting of C1-C6 alkyl, C3-C6 heterocycle, aryl, halo, hydroxy, amino, alkoxy and sulfonyl. Additionally, an alkyl group may contain up to 10 heteroatoms or heteroatom substituents. Suitable heteroatoms include nitrogen, oxygen, sulfur and phosphorous.

As used in this specification, aryl groups are aryl radicals which may contain up to 10 heteroatoms. An aryl group may also be optionally substituted one or more times with an aryl group or a lower alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

As used in this specification, a ring is defined as having up to 20 atoms that may include one or more nitrogen, oxygen, sulfur or phosphorous atoms, provided that the ring can have one or more substituents selected from the group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that the ring may also contain one or more fused rings, including carbocyclic, heterocyclic, aryl, or heteroaryl rings.

General Description:

According to one aspect of the present invention, an amino amide, a peptide or a peptidomimetic (e.g., 5) is prepared by means of the sequential or iterative combination of three steps. Step A involves the conversion of an amine, amino amide or peptide derivative (e.g., 1) to a glyoxamide (e.g., 2). Step B involves the one-step three component reaction among a glyoxamide (e.g., 2), an amine or amino amide (e.g., 3) and an organoboron derivative (e.g., 4). Step C involves the removal of one or both substituents of the amine moiety of amino amide product (or peptide or peptidomimetic) to give a new product (e.g., 6) directly or after the incorporation of an alternative amine substituent. Iterative application of the same steps extends the peptide chain, while the use of alternative components for the three-component step B leads to peptidomimetics.

Amino Amides:

In one aspect, the methods of the invention can be used for the synthesis of amino amides of formula 5 or formula 6.

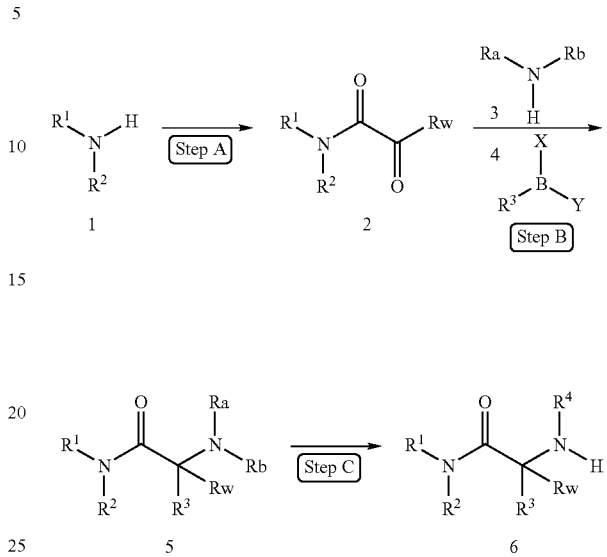

In these methods, $R^1$, $R^2$ and $R^4$ are independently selected from a group consisting of hydrogen, alkyl, allyl, alkenyl, aryl, heteroaryl, acyl, sulfonyl, amino, alkylamino, dialkylamino, acylamino, sulfonylamino, and alkoxy. In some embodiments, $R^1$ and $R^2$ can be connected together forming a ring. $R^3$ can be alkyl, aryl, heteroaryl, allyl, alkenyl, alkynyl, or allenyl. Rw can be hydrogen, alkyl, aryl or heteroaryl. Ra and Rb are independently selected from a group consisting of hydrogen, alkyl, allyl, benzyl, aryl, heteroaryl, acyl, sulfonyl, amino, alkylamino, dialkylamino, acylamino, sulfonylamino, and alkoxy. In some embodiments, Ra and Rb can be joined together forming a ring. X and Y are independently selected from a group consisting of hydroxy, alkoxy, aryloxy, amino, alkylamino, and dialkylamino. In some embodiments, X and Y can be joined together forming a ring. In some embodiments, $R^1$, $R^2$, $R^3$, Ra, Rb, Rw, X or Y can also be connected to a polymeric chain or other solid phase material.

Step A, the conversion of an amine 1 to a glyoxamide derivative 2, can be done in a variety of ways. For example, as shown in Scheme 2, this transformation can be done by converting the amine 1 to an alkenylamide 18, via an acylation reaction with a suitable derivative of the corresponding alkenyl carboxylic acid, followed by ozonolysis. Alternatively, acylation of 1 with a diol acid can form diol amide 19, which can be subjected to periodate cleavage to form glyoxamide 2. This variation has the advantage that it avoids ozonolysis, making it suitable for solid phase synthesis and for molecules containing C=C bonds. Another approach for converting 1 to 2 involves the formation of a functionalized glycolamide 20 (e.g., W=Br, OH), followed by oxidation to form 1. A typical conversion of an amine to a glyoxamide is the conversion of 21 to 24 via 22 or the tartaric acid derivative 23 (Scheme 2).

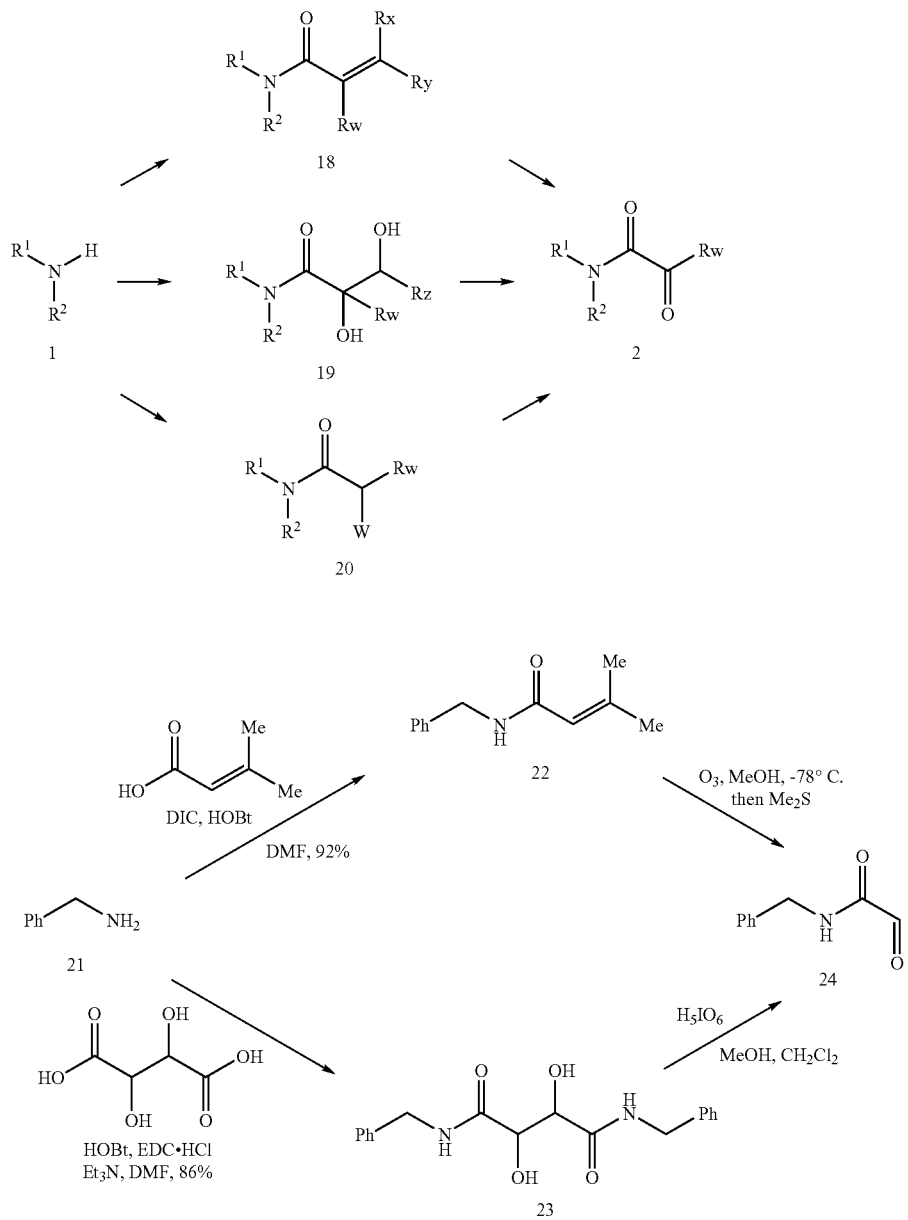

These methods for glyoxamide synthesis are also applicable for similar transformations on amino amides or peptides. More substituted ketoamide derivatives can be generated similarly by using alpha-substituted alkenyl amides or alpha-substituted diolamides, or using other known methods, and can be used in the place of glyoxamides, leading to even more substituted products.

Step B involves the one-step three-component reaction among the glyoxamide 2 (which can be used directly from Step A without further purification), an amine 3 and a boronic acid or related organoboron derivative 4. A related one-step three-component transformation is discussed in more detail in U.S. Pat. No. 6,232,467, which is incorporated by reference herein.

Some examples are shown in Scheme 3. A variety of solvents can be used for this transformation, such as dichloromethane, methanol, ethanol, acetonitrile as well as water or aqueous mixtures. A variety of amine components can be used in Step B, including primary or secondary amines, amino alcohols, hydrazine or hydroxylamine derivatives, amide or sulfonamide derivatives, as well as amino acids, amino esters, amino amides or peptides. The organoboron compound in Step B can be a boronic acid or boronate, as well as a derivative of boronic acid with amines, diamines, amino alcohols or diols. By using chiral amines or chiral organoboron derivatives the product of this process can be obtained with high stereochemical purity.

Scheme 3

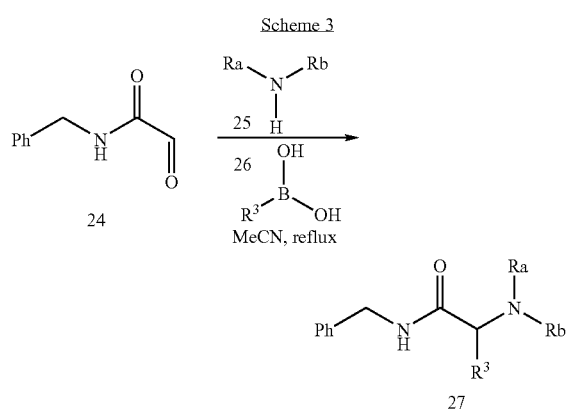

Step C involves the removal of one or both amine substituents in the amine component of Step B and may include the subsequent introduction of other desired amine substituents using typical amine chemistry, including alkylation, reductive amination, amide or sulfonamide bond formation, etc. In this fashion, a wide range of amino amide derivatives can be formed. For example, as illustrated in Scheme 4, the use of benzyl or dibenzyl amines in Step B, can be followed by a de-benzylation step of the resulting products, such as 28, involving catalytic hydrogenation or other methods, leading to amine amides 29. Alternatively, benzhydryl amine adducts (e.g., by using 4,4'-dimethoxy-benzhydrylamine) such as 30, can produce 29 by acid-mediated removal of the benzhydryl group. The use of allyl or diallylamines in Step B gives compounds such as 31, which can be subjected to known deallylation processes (e.g., Pd-catalysis) (Garro-Helion, F.; Merzouk, A.; Guibé, F. J. Org. Chem., 58:6109, 1993) either completely to form 29 or under milder conditions to give mono-deallylated products 32. This approach is more suitable for solid phase synthesis and combinatorial chemistry. A typical example is shown in Scheme 4. Finally, amino amides 29 can be further functionalized to form amino amides 33.

Scheme 4

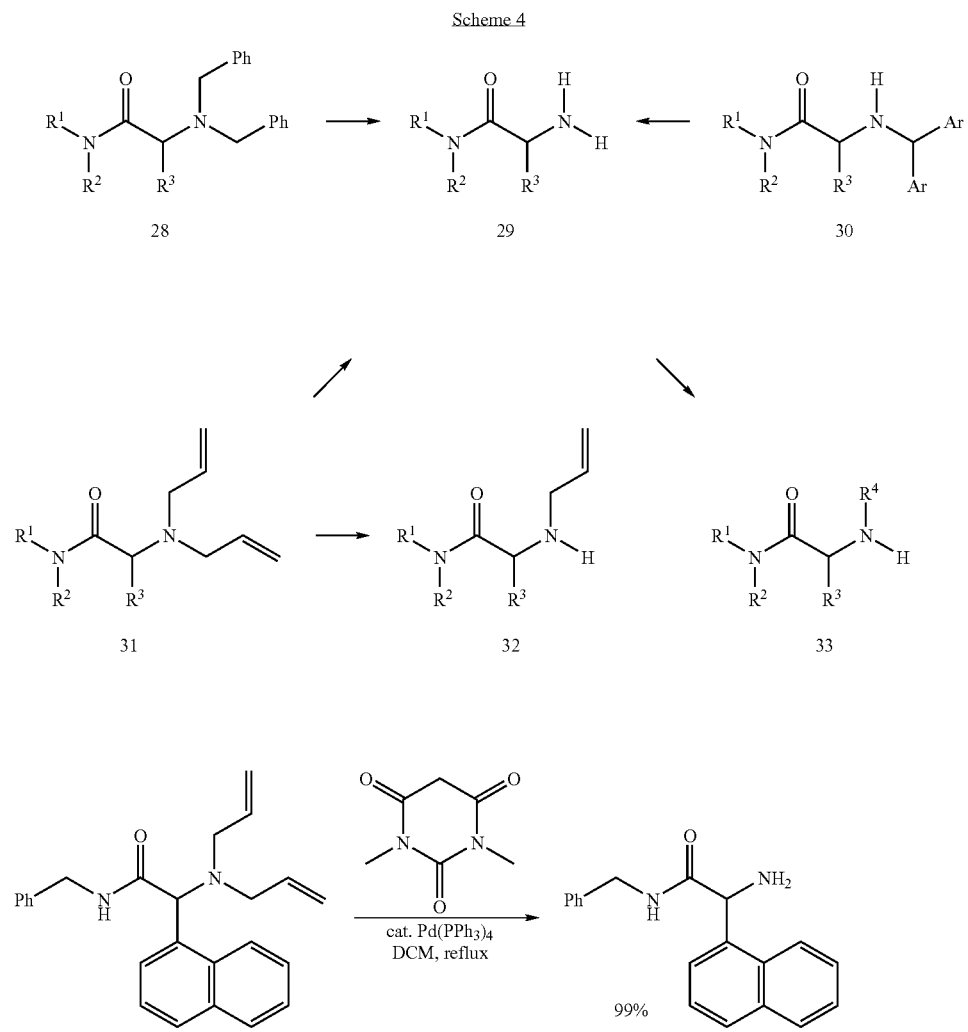

Peptides:

In another aspect, the present invention features methods of preparing a peptide of formula 10 or of formula 11. In Step A, an amino amide derivative 6 is converted to a glyoxamide intermediate 7 which is reacted in Step B with an amine 8 and an organoboron derivative 9 to form dipeptide 10. The use of a primary amine 8 having Rc=$R^6$ and Rd=H gives peptide 11. Alternatively, compound 11 is produced in Step C from compound 10 via the removal of one or both substituents Rc and Rd, followed by the incorporation of $R^6$.

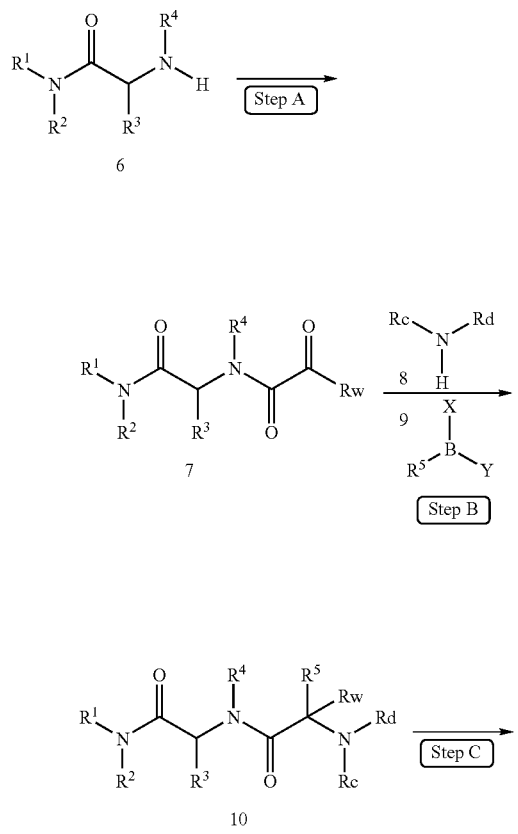

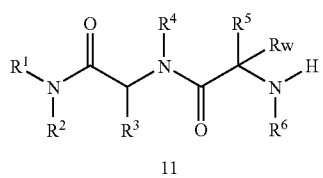

In these methods, $R^1$, $R^2$, $R^4$ and $R^6$ are independently selected from a group consisting of hydrogen, alkyl, allyl, alkenyl, aryl, heteroaryl, acyl, sulfonyl, amino, alkylamino, dialkylamino, acylamino, sulfonylamino, and alkoxy. Rw can be hydrogen, alkyl, aryl or heteroaryl. In some embodiments, two or more of $R^1$, $R^2$, $R^4$ and $R^6$ can be connected together forming one or more rings. $R^3$ and $R^5$ are independently selected from a group consisting of alkyl, aryl, heteroaryl, allyl, alkenyl, alkynyl, and allenyl. Rc and Rd are independently selected from a group consisting of hydrogen, alkyl, allyl, benzyl, aryl, heteroaryl, acyl, sulfonyl, amino, acylamino, sulfonylamino, and alkoxy. In some embodiments, Rc and Rd can be joined together forming a ring. X and Y are independently selected from a group consisting of hydroxy, alkoxy, aryloxy, amino, alkylamino, or dialkylamino. In some embodiments, X and Y can be joined together forming a ring. In some embodiments, $R^1$, $R^2$, $R^3$, $R^4$, $R^5$, Rc, Rd, Rw, X or Y can also be connected to a polymeric chain or other solid phase material.

By combining the synthesis of an amino amide with its conversion to a peptide through the iterative use of Steps A-C, it is possible to produce peptides of highly diverse structures, including the incorporation of unnatural amino acid units. Scheme 5 shows an illustrative example of the conversion of amine 34 to amino amides 35 and 36, followed by the conversion of 36 to dipeptide 37 and 38.

Scheme 5

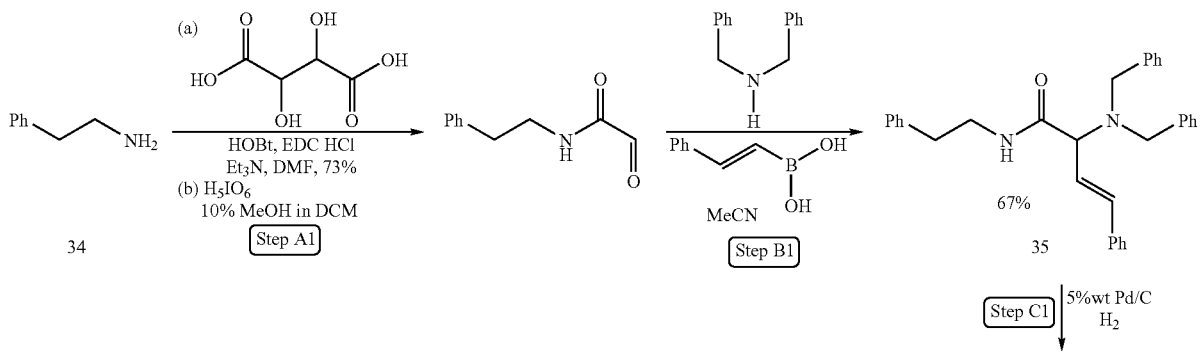

-continued
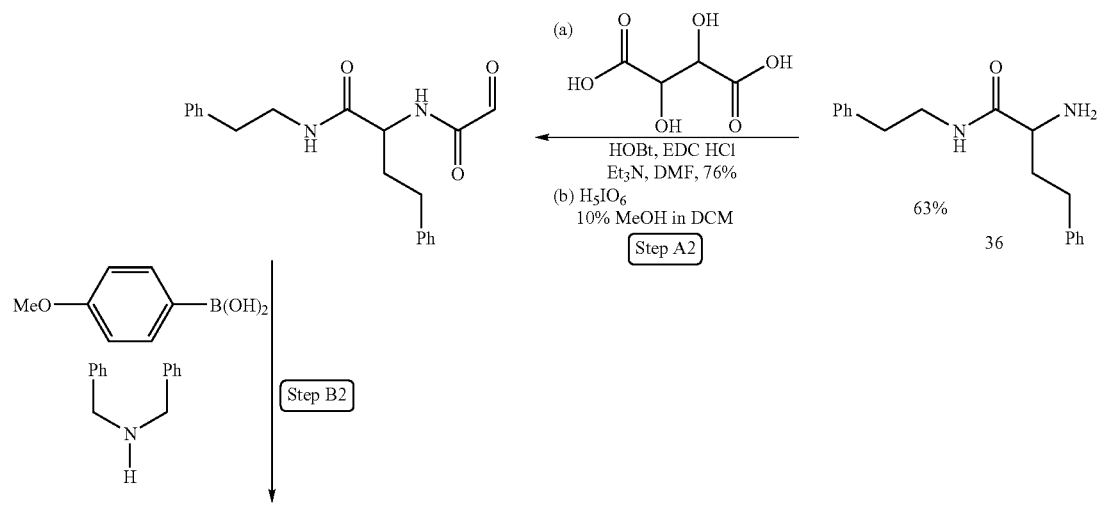
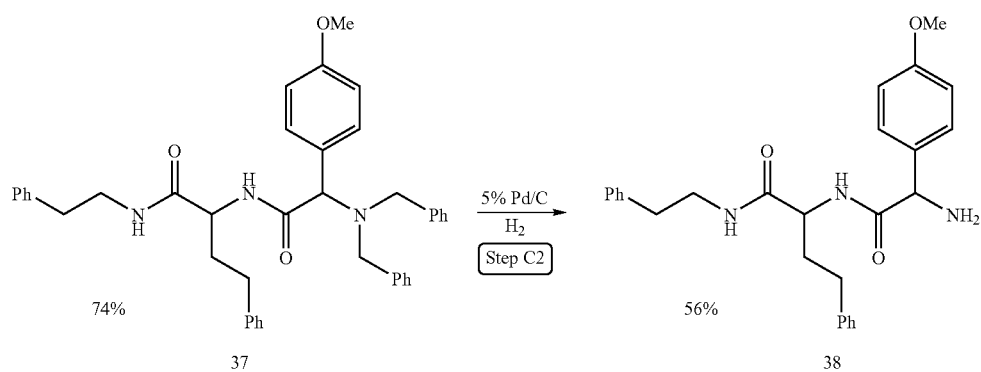
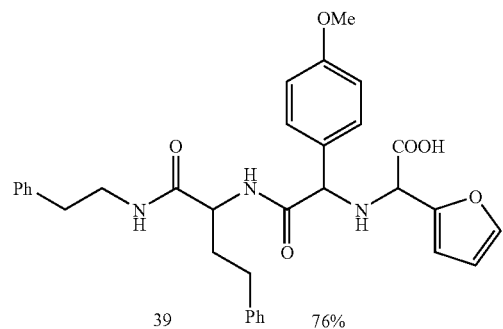

Peptidomimetics:

In another aspect, the present invention features methods of preparing a peptidomimetic of formula 14. An amino amide (or peptide) derivative 6 is reacted with a 1,2-dicarbonyl compound 13 and an organoboron derivative 12 to form peptidomimetic 14. An example is the conversion of 38 to 39 (Scheme 5).

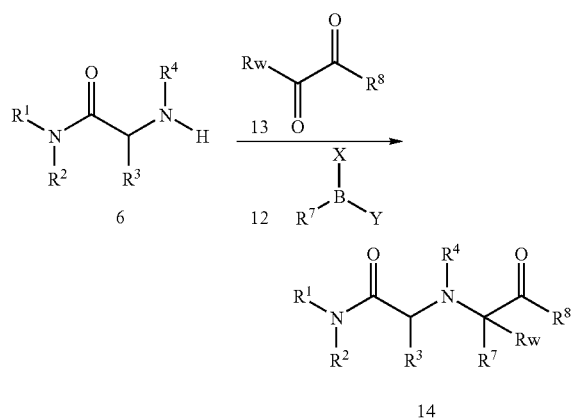

In these methods, $R^1$, $R^2$, and $R^4$ are independently selected from a group consisting of hydrogen, alkyl, allyl, alkenyl, aryl, heteroaryl, acyl, sulfonyl, amino, alkylamino, dialkylamino, acylamino, sulfonylamino, and alkoxy. In some embodiments, two or more of $R^1$, $R^2$, $R^3$ and $R^4$ can be connected together forming one or more rings. Rw can be hydrogen, alkyl, aryl or heteroaryl. $R^8$ can be hydrogen, alkyl, alkenyl, aryl, heteroaryl, amino, alkylamino, dialkylamino, hydroxyamino, alkoxyamino, hydroxyl, alkoxy, aryloxy or heteroaryloxy. $R^3$ and $R^7$ are independently selected from a group consisting of alkyl, aryl, heteroaryl, allyl, alkenyl, alkynyl, and allenyl. X and Y are independently selected from a group consisting of hydroxy, alkoxy, aryloxy, amino, alkylamino, and dialkylamino. In some embodiments, X and Y can also be joined together forming a ring. In some embodiments, $R^1$, $R^2$, $R^3$, $R^4$, $R^7$, $R^8$, Rw, X or Y can also be connected to a polymeric chain or other solid phase material.

In another aspect, the present invention features methods of preparing a peptidomimetic of formula 17. An amino amide derivative 6 is converted to a glyoxamide intermediate 7, which is reacted with and a organoboron derivative 15 and an amino carbonyl derivative 16 to form peptidomimetic 17.

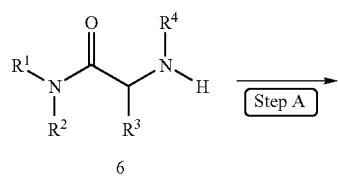

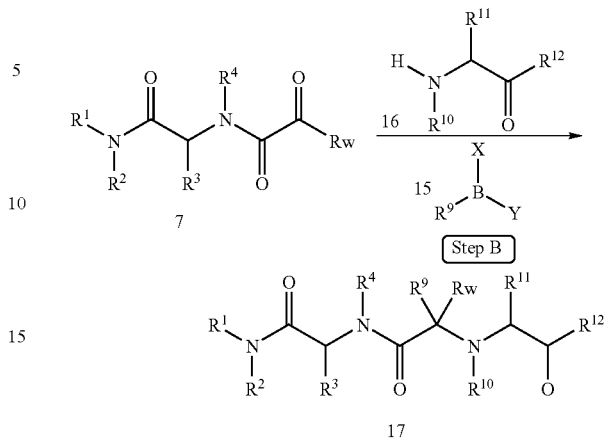

In these methods, $R^1$, $R^2$, $R^4$, and $R^{10}$ are independently selected from a group consisting of hydrogen, alkyl, allyl, alkenyl, aryl, heteroaryl, acyl, sulfonyl, amino, alkylamino, dialkylamino, acylamino, sulfonylamino, and alkoxy. Rw can be hydrogen, alkyl, aryl or heteroaryl. In some embodiments, two or more of $R^1$, $R^2$, $R^3$ and $R^4$ can be connected together forming one or more rings; two or more of $R^{10}$, $R^{11}$ and $R^{12}$ can also be connected together forming one or more rings. $R^3$, $R^9$ and $R^{11}$ are independently selected from a group consisting of alkyl, aryl, heteroaryl, allyl, alkenyl, alkynyl, and allenyl. $R^{12}$ is hydrogen, alkyl, alkenyl, aryl, heteroaryl, amino, alkylamino, dialkylamino, hydroxyamino, alkoxyamino, hydroxyl, alkoxy, aryloxy or heteroaryloxy. X and Y are independently selected from a group consisting of hydroxy, alkoxy, aryloxy, amino, alkylamino, and dialkylamino. In some embodiments, X and Y can also be joined together forming a ring. In some embodiments, $R^1$, $R^2$, $R^3$, $R^4$, $R^9$, $R^{10}$, $R^{11}$, $R^{12}$, Rw, or Y can also be connected to a polymeric chain or other solid phase material.

Solid Phase Synthesis:

The methods of the present invention can be also performed in the solid phase by attaching one of the components on a solid support and by using standard solid phase techniques leading to amino amides, peptides or peptidomimetics after the final cleavage from the solid support. A variety of solid supports and linkers, followed by the appropriate final cleavage procedures can be used for this purpose. Scheme 6 illustrates a solid phase synthesis of a complex amino amide. Rink amine resin 40, is converted to aniline derivative 41 which, according to Step A, is converted to glyoxamide 43 via the oxidation of intermediate glycolamide 42. Performing Step B on 43, followed by cleavage from the resin gives the amino amide product.

Combinatorial Libraries:

Since the process described in this invention involves a multicomponent reaction it allows the direct and rapid generation of combinatorial libraries of the products, by varying the desired substituents. The term "combinatorial library" as used herein refers to a set of compounds that are made by the same process, by varying one or more of the reagents. Combinatorial libraries may be made as mixtures of compounds, or as individual pure compounds, generally depending on the methods used for identifying active compounds. Where the active compound may be easily identified and distinguished from other compounds present by physical and/or chemical characteristics, it may be preferred to provide the library as a large mixture of compounds. Large combinatorial libraries may also be prepared by massively parallel synthesis of individual compounds, in which case compounds are typically identified by their position within an array. Intermediate between these two strategies is "deconvolution", in which the library is prepared as a set of sub-pools, each having a known element and a random element. For example, using the methods of the invention each sub-pool might be prepared from only a single amine (where each sub-pool contains a different amine), but a mixture of different carbonyl derivatives (or organoboron reagents). When a sub-pool is identified as having activity, it is resynthesized as a set of individual compounds (each compound having been present in the original active sub-pool), and tested again to identify the compounds responsible for the activity of the sub-pool.

Such libraries can be generated either in solution or in the solid phase, upon attachment of one substituent onto a solid support. For example, one may couple the starting amine component (e.g., 1, 6) to a substrate through either $R^1$ or $R^2$, convert the amine to one or more glyoxamides/ketoamides, and react the immobilized glyoxamide/ketoamide with a mixture of different organoboron compounds and/or carbonyl compounds to produce a mixture of bound products. Alternatively, the carbonyl compound may be immobilized, and a mixture of organoboron compounds and/or glyoxamides/ketoamides added. Combinatorial libraries may be generated either as individual compounds or as mixtures of compounds.

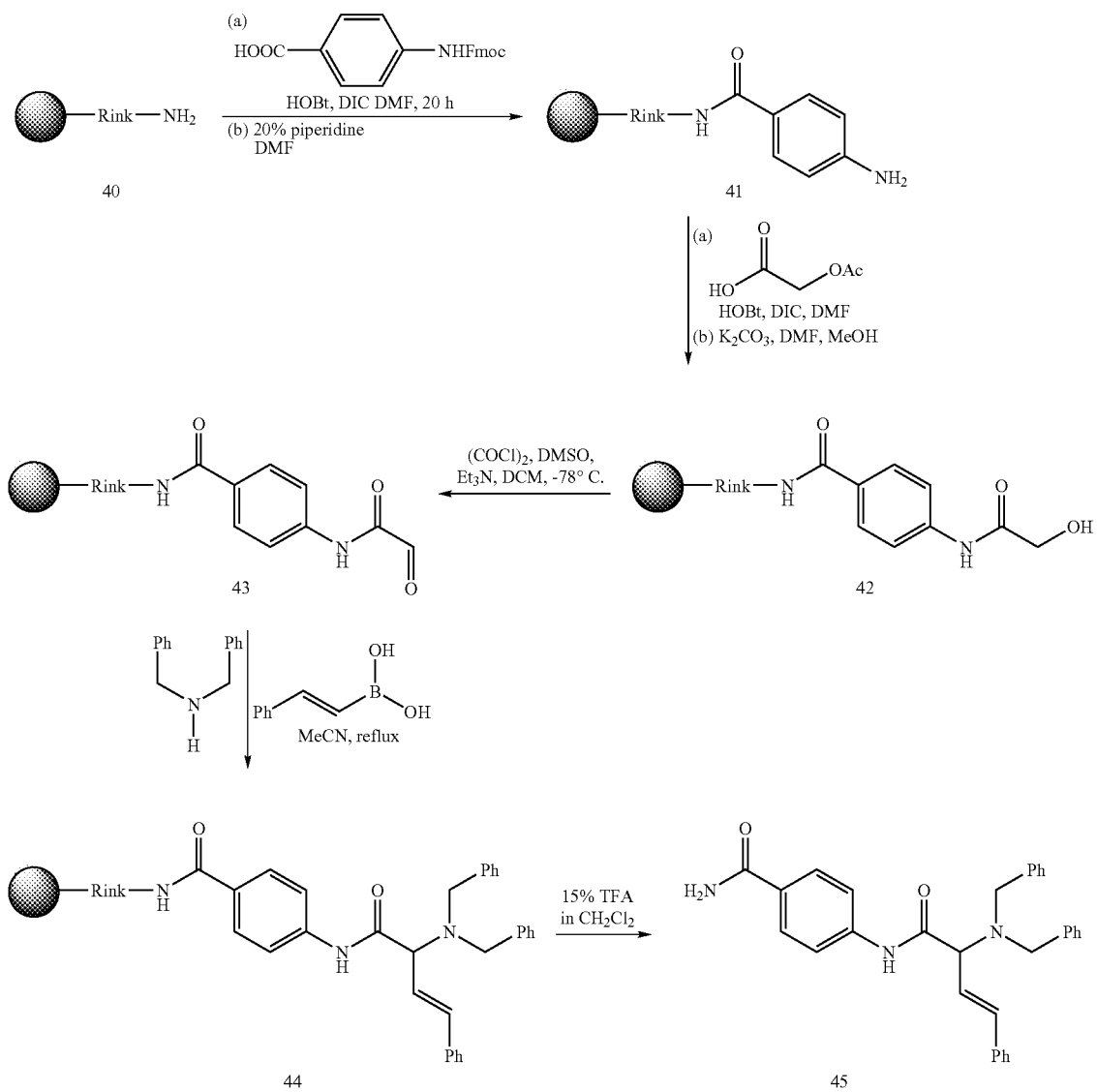

Scheme 6

An illustrative example of a dipeptide having a natural and unnatural amino acid unit is shown in Scheme 7. Beginning with sulfonamide resin 46, the dipeptide 47 is generated, which upon cleavage under standard conditions gives the dipeptide derivative 48. Alternatively, deallylation of 48 gives 49, which can be used in another 3-component process to give peptidomimetic 50. Conversion of 49 to glyoxamide 51 followed by a 3-component process gives dipeptide 52. Further manipulations and/or cleavage from the resin leads to the final-products.

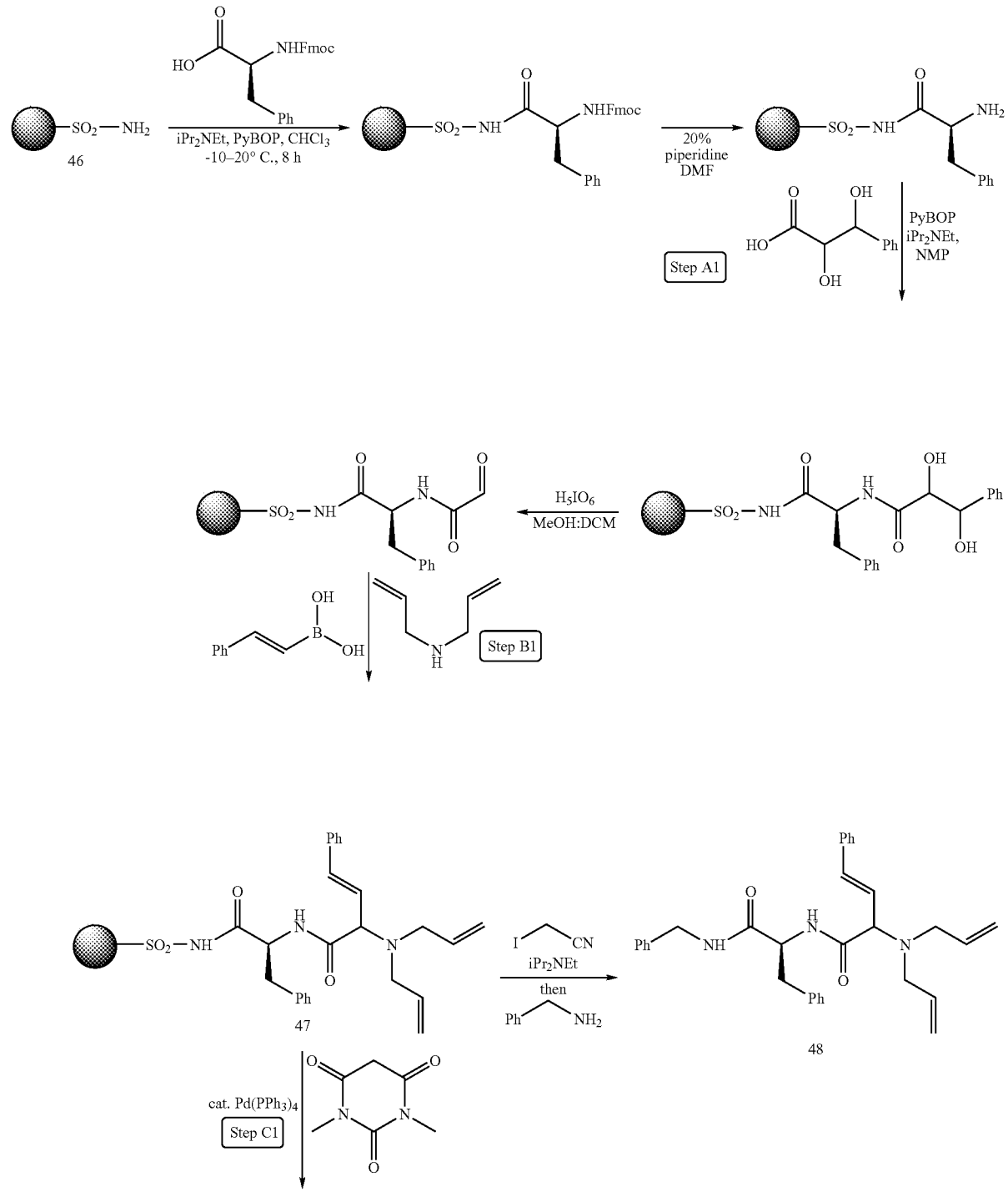

Scheme 7

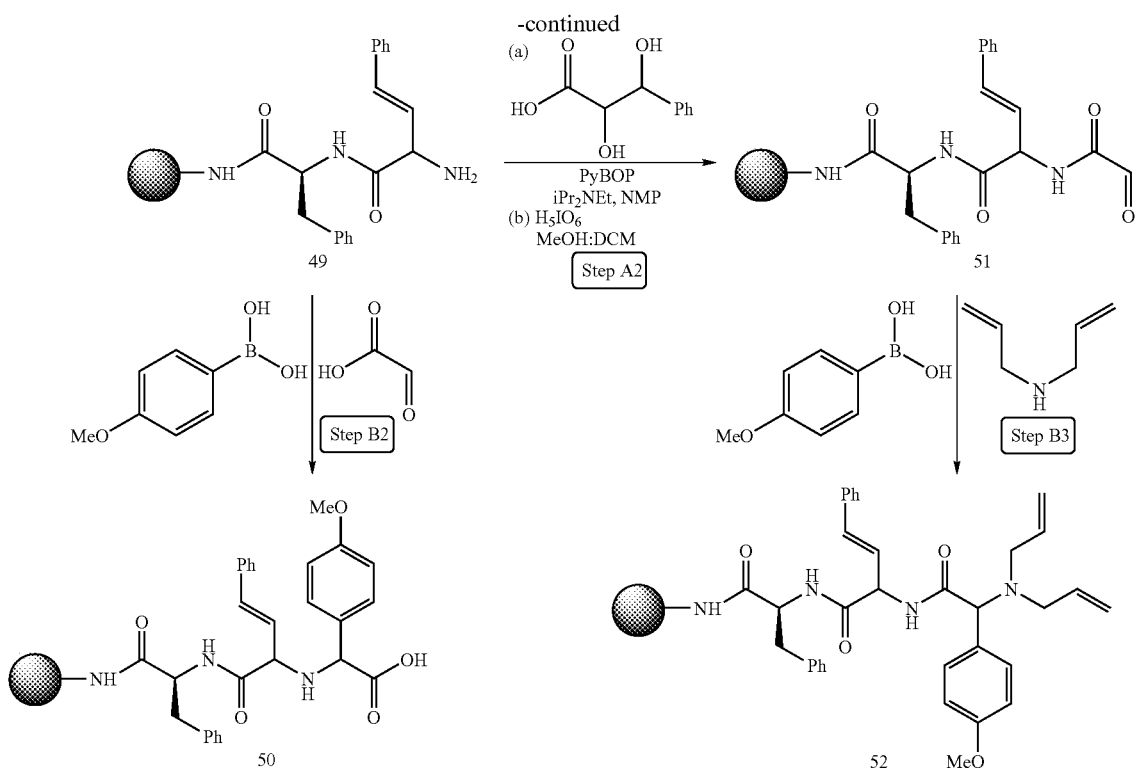

EXAMPLES

The invention will be further described in the following examples, which are illustrative only, and which are not intended to limit the scope of the invention described in the claims.

In the following examples, efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric. Starting materials used in these examples are generally either commercially available or can be readily prepared from commercially available reagents by a procedure involving one or more steps.

Example 1

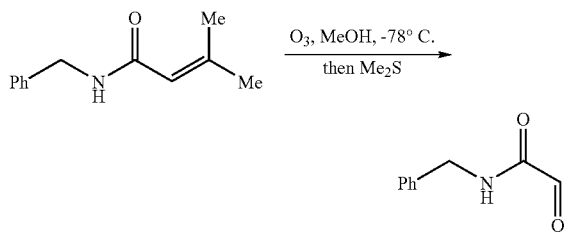

N-Benzyl-3,3-dimethylacrylic amide (830 mg, 4.38 mmol) was dissolved in methanol (15 mL) and cooled to −78° C. Ozone was bubble through this solution until the blue color persisted. After flashing out excess $O_3$ with $O_2$, excess dimethylsulfide was added to the solution. The reaction mixture was gradually warmed up to 0° C. for 1 h and further warmed up to room temperature for 1 h. After removal of volatiles, the residue was chromatographed with hexane-ethyl acetate (50:50) to yield the desired product. The product showed satisfactory spectral data by $H^1$ NMR.

Example 2

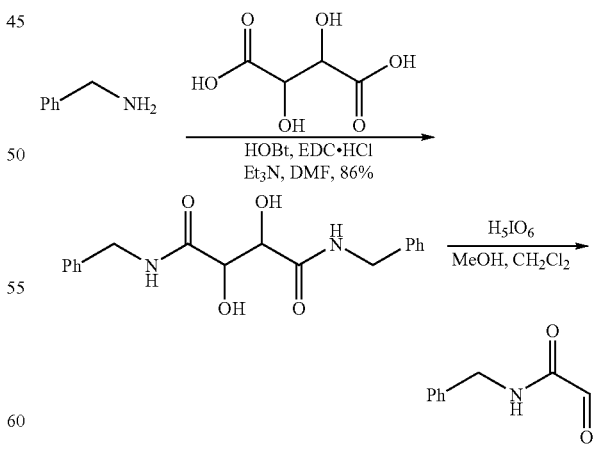

Tartaric acid (694 mg, 4.62 mmol) in DMF (20 mL) was added to benzylamine (1.0 mL, 9.06 mmol), followed by $Et_3N$ (1.27 mL, 9.11 mmol), HOBT (1.225 g, 9.06 mmol), and EDC.HCl (1.773 g, 9.06 mmol). The mixture was stirred at room temperature overnight. Saturated $NaHCO_3$ was added to quench the reaction. The white precipitate was filtered and washed with saturated NaHCO$_3$, EtOAc and Et$_2$O, dried under vacuum (1.275 g, 86% yield). The resulting N,N'-Dibenzyl-2,3-dihydroxy-succinamide (328 mg, 1.0 mmol) was suspended in 10% MeOH in DCM (5 mL), and H$_5$IO$_6$ (230 mg, 1.0 mmol) was added. The reaction mixture was stirred at room temperature for 1 h. The white solid was filtered and washed with DCM. To the filtered organic solution was added H$_2$O, after separation the organic layer, the aqueous layer was extracted with DCM several times. The combined organic layer was then dried over MgSO$_4$, and evaporated to get crude product without further purification.

Example 3

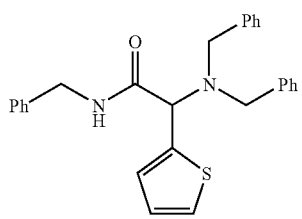

To a solution of N-benzyl glyoxyamide (prepared according to Example 1 or 2) in acetonitrile, was added dibenzylamine (1.05 equivalent) and 2-thiopheneboronic acid (1.05 equivalent), and the reaction mixture was refluxed overnight. After it was diluted with EtOAc, the mixture was washed with 0.1N NaOH, brine, and dried over MgSO$_4$. The residue was purified by flash chromatography giving the product in 55% yield. $^1$H NMR (360 MHz, CDCl$_3$) δ 7.42-7.16 (m, 16H), 7.05 (dd, J=5.1, 3.5 Hz, 1H) 7.02-6.99 (m, 1H), 4.69 (s, 1H), 4.60-4.40 (m, 2H), 3.80 (d, J=13.6 Hz, 2H), 3.39 (d, J=13.6 Hz, 2H); $^{13}$C NMR (63 MHz, CDCl$_3$) δ 170.2, 138.4, 138.1, 135.8, 128.7, 128.6, 128.6, 127.8, 127.6, 127.4, 126.4, 125.8, 62.6, 54.6, 43.6.

Example 4

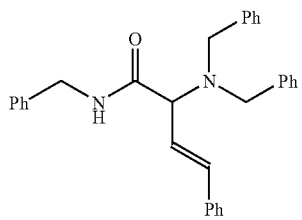

Prepared similarly to Example 3 in 70% yield. $^1$H NMR (250 MHz, CDCl$_3$) δ 7.71-6.93 (m, 20H), 6.51 (d, J=15.9 Hz, 1H), 6.36 (dd, J=15.9, 8.9 Hz, 1H), 4.59-4.33 (m, 2H), 3.87 (d, J=8.9 Hz, 1H), 3.81 (d, J=13.5 Hz, 2H), 3.31 (d, J=13.5 Hz, 2H); $^{13}$C NMR (63 MHz, CDCl$_3$) δ 171.9, 138.5, 138.3, 137.1, 136.4, 128.8, 128.7, 128.6, 128.5, 128.0, 127.7, 127.5, 127.4, 126.7, 122.2, 65.7, 54.7, 43.4.

Example 5

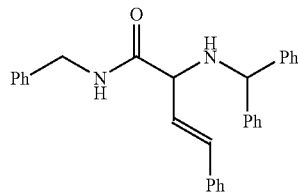

Prepared similarly to Example 3 in 91% yield. $^1$H NMR (360 MHz, CDCl$_3$) δ 7.45-6.87 (m, 20H), 6.47 (d, J=15.6 Hz, 1H), 6.17 (dd, J=15.6, 7.6 Hz, 1H), 4.84 (s, 1H), 4.52-4.32 (m, 2H), 3.80 (d, J=7.6 Hz, 1H); $^{13}$C NMR (63 MHz, CDCl$_3$) δ 171.7, 142.8, 142.6, 138.1, 136.1, 133.3, 128.5, 128.4, 127.8, 127.5, 127.3, 127.2, 126.5, 126.4, 64.4, 62.6, 43.1.

Example 6

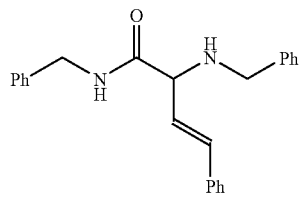

Prepared similarly to Example 3 in 67% yield. $^1$H NMR (360 MHz, CDCl$_3$) δ 7.54-7.06 (m, 15H), 6.60 (d, J=15.7 Hz, 1H), 6.18 (dd, J=15.7, 7.6 Hz, 1H), 4.51-4.33 (m, 2H), 3.89 (d, J=7.6 Hz, 1H), 3.81-3.67 (m, 2H); $^{13}$C NMR (90 MHz, CDCl$_3$) δ 171.6, 139.1, 138.2, 136.1, 133.1, 128.5, 128.4, 128.0, 127.8, 127.5, 127.3, 127.1, 126.6, 126.4, 64.6, 51.8, 43.1.

Example 7

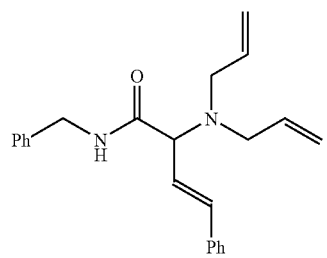

Prepared similarly to Example 3 in 55% yield. $^1$H NMR (360 MHz, CDCl$_3$) δ 7.58-7.10 (m, 10H), 6.49 (d, J=15.4 Hz, 1H), 6.18 (dd, J=15.4, 9.1 Hz, 1H), 5.78-5.60 (m, 2H), 5.18-5.03 (m, 4H), 4.53-4.30 (m, 2H), 3.94 (d, J=9.1 Hz, 1H), 3.27-3.15 (m, 2H), 2.99-2.88 (m, 2H); $^{13}$C NMR (90 MHz, CDCl$_3$) δ 171.9, 138.3, 136.3, 136.2, 134.9, 128.5, 128.3, 127.7, 127.5, 127.2, 126.4, 122.7, 118.0, 66.7, 53.4, 43.1.

Example 8

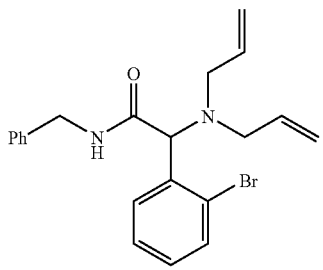

Prepared similarly to Example 3 in 42% yield. ¹H NMR (360 MHz, CDCl₃) δ 7.68-7.06 (m, 9H), 5.88-5.63 (m, 2H), 5.15-5.05 (m, 4H), 4.93 (s, 1H), 4.55-4.39 (m, 2H), 3.29-3.07 (m, 4H); ¹³C NMR (90 MHz, CDCl₃) δ 171.1, 138.1, 136.0, 134.5, 133.2, 130.6, 129.3, 128.5, 127.6, 127.3, 127.2, 125.9, 117.9, 68.6, 53.2, 43.2.

Example 9

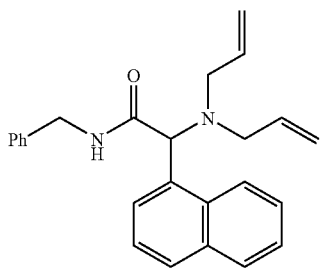

Prepared similarly to Example 3 in 57% yield. ¹H NMR (250 MHz, CDCl₃) δ 8.35-8.21 (m, 1H), 7.90-7.73 (m, 2H), 7.63-7.11 (m, 9H), 5.86-5.65 (m, 2H), 5.19 (s, 1H), 5.17-5.00 (m, 4H), 4.56-4.32 (m, 2H), 3.39-3.08 (m, 4H); ¹³C NMR (63 MHz, CDCl₃) δ 172.0, 138.2, 134.9, 134.0, 132.7, 132.5, 128.7, 128.6, 128.5, 127.6, 127.3, 127.0, 126.2, 125.6, 125.0, 124.0, 118.0, 65.9, 53.4, 43.2.

Example 10

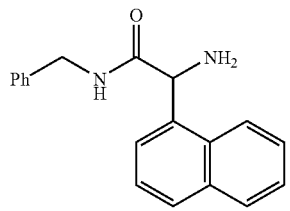

The product of Example 9 (95 mg, 0.26 mmol) was placed in a 10 mL vacuum dried flask containing, Pd(PPh₃)₄ (6 mg), and N,N-dimethyl barbituric acid (243 mg, 1.54 mmol). Dichloromethane (1.5 mL) was added and the reaction mixture was refluxed for 6 h. A large amount of EtOAc was added, washed with aqueous Na₂CO₃ several times. The organic layer was dried over MgSO₄. After the removal of volatiles, the residue was flash chromotographied with 2% MeOH in DCM to obtain product (74 mg, 99% yield). ¹H NMR (360 MHz, CDCl₃) δ 8.20-7.04 (m, 13H), 5.08 (s, 1H), 4.48-4.29 (m, 2H); ¹³C NMR (90 MHz, CDCl₃) δ 173.2, 138.2, 134.0, 131.9, 131.8, 128.8, 128.5, 128.4, 127.6, 127.2, 126.4, 125.7, 125.3, 125.1, 123.4, 56.6, 43.1.

Example 11

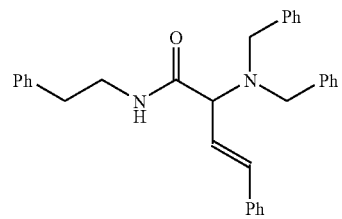

Prepared similarly to Example 3 in 67% yield. ¹H NMR (360 MHz, CDCl₃) δ 7.40-7.03 (m, 20H), 6.40 (d, J=16.3 Hz, 1H), 6.24 (dd, J=16.3, 9.3 Hz, 1H), 3.75-3.57 (m, 5H), 3.52-3.40 (m, 1H), 3.32 (d, J=13.7 Hz, 2H), 2.86-2.66 (m, 2H); ¹³C NMR (63 MHz, CDCl₃) δ 171.6, 138.5, 138.3, 136.6, 136.1, 128.5, 128.4, 128.3, 128.2, 128.1, 127.8, 127.6, 127.0, 126.6, 126.4, 126.4, 65.5, 54.3, 52.8, 39.7, 35.2.

Example 12

To the solution of the product of Example 11 (451 mg, 0.98 mmol) in EtOAc-MeOH 1:1 (20 mL) was added 5% wt Pd/C (266 mg). The reaction mixture was stirred under the atmosphere of hydrogen gas until all the starting material was consumed, then filtered through celite pad and volatiles were removed. Pure product was isolated by flash chromatography using 10% MeOH in DCM as an eluent (174 mg, 63% yield). ¹H NMR (250 MHz, CDCl₃) δ 7.67-7.07 (m, 10H), 3.54 (dd, J=13.3, 7.0 Hz, 2H), 3.42-3.27 (m, 1H), 2.84 (t, J=7.0 Hz, 2H), 2.76-2.63 (m, 2H), 2.28-2.07 (m, 1H) 1.90-1.67 (m, 3H); ¹³C NMR (90 MHz, CDCl₃) δ 174.5, 141.0, 138.8, 128.5, 128.4, 128.3, 128.2, 126.2, 125.8, 54.5, 40.0, 36.4, 35.6, 31.8.

Example 13

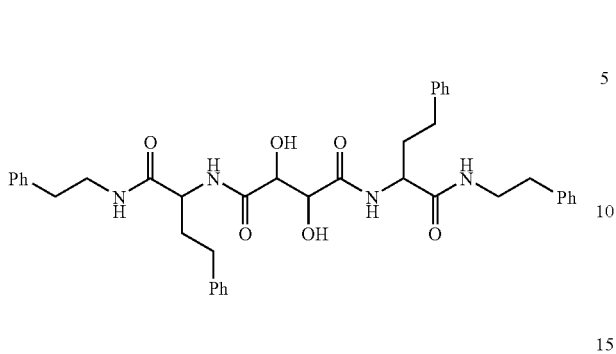

Prepared similar to Example 2 from the product of Example 12 in 76% yield. $^1$H NMR (360 MHz, MeOD-d$_4$) δ 7.39-6.93 (m, 20H), 4.56-4.47 (m, 2H), 4.44-4.33 (m, 2H), 3.56-3.27 (m, 4H), 2.88-2.74 (m, 4H), 2.72-2.49 (m, 4H), 2.24-1.81 (m, 4H); $^{13}$C NMR (90 MHz, MeOD-d$_4$) δ 174.6, 174.3, 174.2, 173.9, 142.5, 142.2, 140.3, 129.8, 129.5, 129.5, 129.4, 127.4, 127.1, 127.0, 74.7, 74.2, 54.2, 54.0, 42.0, 41.9, 36.4, 36.3, 35.9, 35.9, 35.0, 32.9, 32.7.

Example 14

The product of Example 13 was converted to the corresponding glyoxamide similarly to Example 2, and reacted with p-methoxyphenyl boronic acid and dibenzylamine, similarly to Example 3. The dipeptide product was obtained in 74% overall yield, containing a mixture of two diastereomers. $^1$H NMR (250 MHz, CDCl$_3$) δ 8.40-8.08 (m, 1H), 7.56-6.72 (m, 25H), 4.71-4.55 (m, 1H), 4.40 (s, 1H), 3.91-3.76 (m, 2H), 3.75 (s, 3H), 3.58-3.13 (m, 4H), 2.70-2.43 (m, 4H), 2.25-1.83 (m, 2H); $^{13}$C NMR (63 MHz, CDCl$_3$) δ 171.6, 171.5, 171.0, 170.9, 159.1, 140.9, 138.7, 138.2, 138.1, 131.6, 131.5, 129.0, 128.6, 128.5, 128.2, 128.1, 127.3, 126.1, 125.8, 125.2, 125.1, 113.4, 66.9, 66.9, 55.0, 54.5, 54.4, 52.6, 52.5, 40.5, 40.5, 35.3, 35.2, 34.8, 31.6, 31.2.

Example 15

Prepared from the product of Example 14 similarly to Example 12 in 56% yield containing two diastereomers. Diatereomer A: $^1$H NMR (360 MHz, MeOD-d$_4$) δ 7.51-6.73 (m, 14H), 4.46 (s, 1H), 4.28 (dd, J=8.3, 5.4 Hz, 1H), 3.73 (s, 3H), 3.42-3.24 (m, 2H), 2.67 (t, J=7.4 Hz, 2H), 2.63-2.43 (m, 2H), 2.08-1.79 (m, 2H); $^{13}$C NMR (90 MHz, MeOD-d$_4$) δ 175.8, 173.6, 160.9, 142.3, 140.2, 134.2, 129.8, 129.6, 129.5, 129.4, 129.1, 127.4, 127.0, 115.1, 59.7, 55.7, 54.2, 41.8, 36.3, 35.2, 32.9; Diastereomer B: $^1$H NMR (360 MHz, MeOD-d$_4$) δ 7.52-6.72 (m, 14H), 4.48 (s, 1H), 4.18 (dd, J=9.5, 4.6 Hz, 1H), 3.72 (s, 3H), 3.48-3.31 (m, 2H), 2.76 (t, J=7.3 Hz, 2H), 2.46-2.25 (m, 2H), 2.04-1.71 (m, 2H); $^{13}$C NMR (63 MHz, MeOD-d$_4$) δ 175.8, 173.9, 160.9, 142.0, 140.3, 134.3, 129.8, 129.5, 129.4, 129.3, 129.2, 127.3, 127.0, 115.1, 59.4, 55.7, 54.1, 41.9, 36.4, 35.0, 32.7.

Example 16

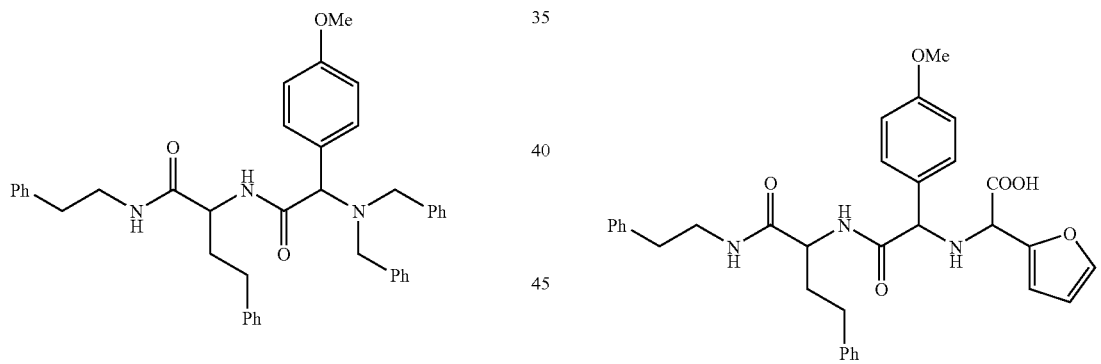

One of the diastereomers of Example 15 (47 mg, 0.10 mmol) was dissolved in a mixture of DCM and MeOH (1:1, 3 mL), and mixed with glyoxylic acid monohydrate (11 mg, 0.12 mmol), followed by the addition 2-furanboronic acid (13 mg, 0.12 mmol). The reaction mixture was stirred at room temperature for 22 h. After removal of the volatiles, the crude product was purified by EtOAc:MeOH:NH$_4$OH (8:2:0.5) as eluent (47 mg, 76% yield) containing two diastereomers. $^1$H NMR (360 MHz, MeOD-d$_4$) δ 7.56-6.73 (m, 15H), 6.47-6.24 (m, 2H), 4.54 (s, 0.4H), 4.46 (s, 0.6H), 4.38 (s, 0.4H), 4.31 (s, 0.6H), 4.23-4.14 (m, 1H), 3.75 (s, 1.8H), 3.74 (s, 1.2H), 3.48-3.31 (m, 2H), 2.82-2.66 (m, 2H), 2.51-2.26 (m, 2H), 2.05-1.71 (m, 2H); $^{13}$C NMR (90 MHz, MeOD-d$_4$) δ 174.3, 173.9, 173.8, 173.8, 173.2, 173.0, 161.6, 152.7, 143.8, 142.0, 140.3, 130.5, 129.8, 129.5, 129.4, 129.4, 127.3, 127.0, 64.8, 64.3, 60.3, 60.1, 55.8, 54.2, 42.0, 36.2, 35.0, 32.8, 32.7.

Example 16

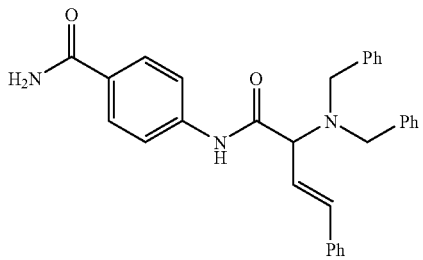

Part 1: To a mixture of Rink amine resin (503 mg, 0.10 mmol) in DMF (4 mL) was added N-Fmoc-4-aminobenzoic acid (111 mg, 0.30 mmol), DIC (N,N'-diisopropylcarbodiimide) (48 µL, 0.30 mmol), and HOBT (1-hydroxybenzotriazole) (41 mg, 0.30 mmol). The mixture was stirred at room temperature overnight under argon. The resin was filtered off and washed repeated with DMF, MeOH and DCM. The resin was then treated with 20% piperidine in DMF for half an hour, filtered off and washed repeatly with DMF, MeOH and DCM, dried under vacuum.

Part 2: The resin from Step 1 was swelled in DMF (4 mL) and reacted with acetoxyacetic acid (36 mg, 0.30 mmol), DIC (48 mL, 0.30 mmol), and HOBT (41 mg, 0.30 mmol). The mixture was stirred for 16 h. The resin was filtered off and washed repeatly with DMF, MeOH and DCM. To the acylated resin in DMF (3 mL) and MeOH (1.5 mL) was added $K_2CO_3$ (139 mg, 1.0 mmol), and the mixture was stirred at room temperature for 22 h. The resin was filtered off and washed repeatly with $H_2O$, MeOH and DCM, dried under vacuum.

Part 3: To the solution of oxalyl chloride (27 µL, 0.30 mmol) in DCM (1 mL) was added dimethyl sulfoxide (43 µL, 0.60 mmol) at –78° C., and the mixture was stirred for 30 min. To this solution was added the glycolamide resin from Part 2 diluted with DCM (2 mL). The mixture was stirred at –78° C. for 1 h, and reacted with $Et_3N$ (0.11 mL, 0.77 mmol) and allowed to warm up to room temperature for 2 h. The resin was filtered off, washed with DCM.

Part 4: Acetonitrile (4 mL) was added to the resin from Part 4, followed by the addition of dibenzylamine (45 mL, 0.23 mmol), and (E)-styrylboronic acid (34 mg, 0.23 mmol). The mixture was refluxed for 17 h. After cooling to room temperature, the resin was filtered off, washed with MeOH, DCM, and then cleaved with 15% TFA in DCM for 1 h. The resin was filtered off and washed with MeOH, DCM. The solution was evaporated (co-evaporate with toluene). The residue was dissolved in DCM, neutralized with $Et_3N$, and evaporated. The crude mixture was purified by flash chromatography with gradient mixture of MeOH and DCM giving the product (12 mg, 25% yield from the initial loading). $^1$H NMR (500 MHz, MeOD-$d_4$) δ 7.86 (d, J=8.8 Hz, 2H), 7.67 (d, J=8.8 Hz, 2H), 7.50-7.21 (m, 15H), 6.64 (d, J=16.0 Hz, 1H), 6.46 (dd, J=16.0, 8.4 Hz, 1H), 4.06 (d, J=8.4 Hz, 1H), 3.92 (d, J=13.6 Hz, 2H), 3.72 (d, J=13.6 Hz, 2H), $^{13}$C NMR (125 MHz, MeOD-$d_4$) δ 171.3, 171.7, 142.5, 140.2, 137.8, 137.7, 130.3, 130.1, 129.8, 129.7, 129.6, 129.1, 128.4, 127.7, 124.5, 120.3, 68.8, 56.3.

Example 17

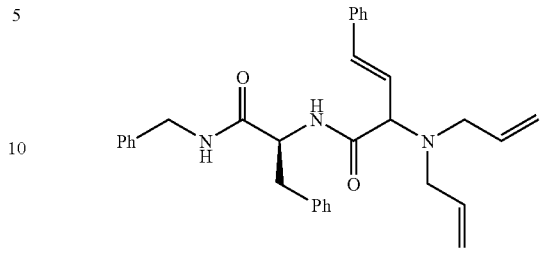

Part 1: To 4-sulfamylbutyryl AM resin (134 mg, 0.15 mmol) were added $CHCl_3$ (1.7 mL), $iPr_2NEt$ (131 µL, 0.75 mmol), and Fmoc-Phe-OH (178 mg, 0.45 mmol). The mixture was stirred for 10 min followed by cooling to –20° C. After 20 min, PyBOP (234 mg, 0.45 mmol) was added to the reaction mixture and stirred for 8 h. The resin was filtered, washed with MeOH, DCM, DMF, and treated with 20% piperidine in DMF (3 mL) for 30 min, The resin was filtered off, washed with DMF, DCM, and dried under vacuum.

Part 2: The resin from Part 1 was swelled in NMP (2 mL) and mixed with 2,3-dihydroxy-3-phenyl-propionic acid (82 mg, 0.45 mmol), $iPr_2NEt$ (131 µL, 0.75 mmol), and PyBOP (234 mg, 0.45 mmol). After stirring at room temperature for 8 h, the resin was filtered off, washed with NMP, MeOH, DCM, and dried under vacuum.

Part 3: The resin from Part 2 (71 mg, 0.059 mmol) was swelled in 10% MeOH in DCM (2 mL), and reacted with $H_5IO_6$ (20 mg, 0.087 mmol). The mixture was stirred for 1 h, and the resin was filtered off, and washed with MeOH and DCM.

Part 4: To the resin from Part 3 were added toluene (1.0 mL), acetonitrile (0.5 mL), diallylamine (25 µL, 0.20 mmol), (E)-styrylboronic acid (30 mg, 0.2 mmol). The reaction mixture was stirred at 55° C. overnight. The resin was filtered off, washed with MeOH, DCM, and dried under vacuum.

Part 5: To the resin from Part 4 were added NMP (1 mL), $iPr_2NEt$ (59 µL, 0.34 mmol), and iodoacetonitrile (101 µL, 1.36 mmol). The reaction mixture was shielded from light, stirred for 24 h, filtered off, and washed with NMP, DCM and THF. To the resulting resin were added THF (1 mL) and benzylamine (7.5 µL, 0.068 mmol). The mixture was stirred for 4 h. The resin was filtered off and washed with MeOH, DCM. The organic solution was evaporated and the residue was purified with 30% EtOAc in hexane to obtain desired product (4 mg, 14% yield calculated from theoretical loading of the initial resin). $^1$H NMR (500 MHz, CDCl$_3$) δ 7.79-7.71 (m, 1H), 7.40-7.04 (m, 16H), 6.48 (d, J=16.0 Hz, 1H), 6.04 (dd, J=16.0, 9.3 Hz, 1H), 5.78-5.60 (m, 2H), 5.25-5.06 (m, 4H), 4.68 (dd, J=15.5, 7.5 Hz, 1H), 4.42-4.28 (m, 2H), 3.89 (d, J=8.8 Hz, 1H), 3.24-3.06 (m, 4H), 2.90 (dd, J=13.9, 7.4 Hz, 2H), $^{13}$C NMR (125 MHz, CDCl$_3$) δ 172.7, 170.6, 136.5, 135.1, 129.3, 129.2, 128.7, 128.6, 128.5, 127.9, 127.6, 127.4, 127.0, 126.6, 122.4, 118.2, 67.0, 54.3, 53.6, 43.5, 37.8

A number of embodiments of the invention have been described. Nevertheless, it will be understood that various modifications may be made without departing from the spirit and scope of the invention. Accordingly, other embodiments are within the scope of the following claims.

What is claimed is:

1. A method for preparing a compound represented by formula 5:

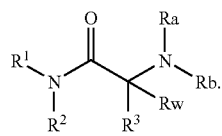

5 comprising the steps of:

(a) converting a compound represented by formula 1 to a compound represented by formula 2:

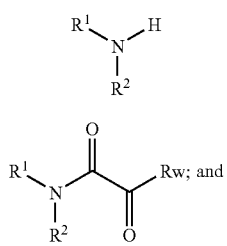

(b) reacting the compound of formula 2 with an amine derivative represented by formula 3 and an organoboron compound represented by formula 4:

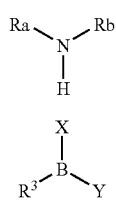 

3

4 thereby forming the compound represented by formula 5, wherein:

$R^1$ and $R^2$ are independently selected from the group consisting of hydrogen, alkyl, allyl, alkenyl, aryl, heteroaryl, acyl, sulfonyl, amino, alkylamino, dialkylamino, acylamino, sulfonylamino, and alkoxy, provided that $R^1$ and $R^2$ can be connected together forming a ring; or $R^2$ is a group represented by the following formula:

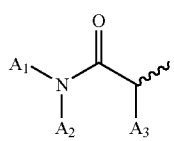

1a wherein:

$A^1$ and $A^2$ are independently selected from the group consisting of hydrogen, alkyl, allyl, alkenyl, aryl, heteroaryl, acyl, sulfonyl, amino, alkylamino, dialkylamino, acylamino, sulfonylamino, alkoxy, an amino acid and a peptide;

$A^3$ is alkyl, aryl, heteroaryl, allyl, alkenyl, alkynyl, or allenyl; and $R^1$, $A^1$, $A^2$ and $A^3$ are optionally connected to form one or more rings;

Rw is hydrogen, alkyl, aryl, or heteroaryl;

Ra and Rb are independently selected from the group consisting of hydrogen, alkyl, allyl, benzyl, aryl, heteroaryl, acyl, sulfonyl, amino, alkylamino, dialkylamino, acylamino, sulfonylamino, and alkoxy, provided that Ra and Rb can be joined together forming a ring; or Ra is hydrogen, alkyl, allyl, alkenyl, aryl, heteroaryl, acyl, sulfonyl, amino, alkylamino, dialkylamino, acylamino, sulfonylamino, or alkoxy and Rb is

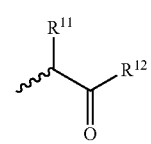

16' wherein $R^{12}$ is selected from the group consisting of hydrogen, alkyl, alkenyl, aryl, heteroaryl, amino, alkylamino, dialkylamino, hydroxyamino, alkoxyamino, hydroxyl, alkoxy, aryloxy and heteroaryloxy;

$R^3$ and $R^{11}$ are independently alkyl, aryl, heteroaryl, allyl, alkenyl, alkynyl, or allenyl;

provided that Ra, $R^{11}$ and $R^{12}$ can be connected together forming one or more rings and X and Y are independently selected from the group consisting of hydroxy, alkoxy, aryloxy, amino, alkylamino, and dialkylamino, provided that X and Y can be joined together forming a ring.

2. The method of claim 1, further comprising: converting the amino amide of formula 5 to an amino amide of formula 6

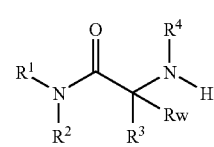

6 wherein:

$R^4$ is hydrogen, alkyl, allyl, alkenyl, aryl, heteroaryl, acyl, sulfonyl, amino, alkylamino, dialkylamino, acylamino, sulfonylamino, or alkoxy.

3. The method of claim 1, wherein one of $R^1$, $R^2$, $R^3$, Ra, Rb, Rw, X and Y is connected to a polymeric chain or other solid phase material.

4. The method of claim 1, wherein the amino amide of formula 5 is formed as a member of a combinatorial library.

5. The method of claim 3, wherein the amino amide of formula 5 is formed as a member of a combinatorial library.

6. The method of claim 1, wherein the compound prepared by the method is represented by formula 17':

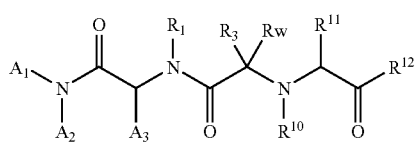

wherein the compound of formula 17' is prepared by
(a) converting a compound represented by formula 1a' to a compound represented by formula 2a':

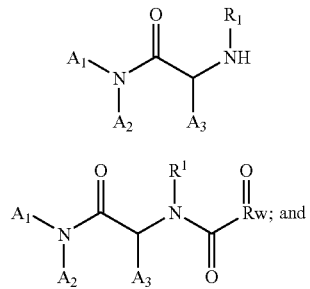

(b) reacting the compound of formula 2a' with an amine derivative represented by formula 3' and an organoboron compound represented by formula 4:

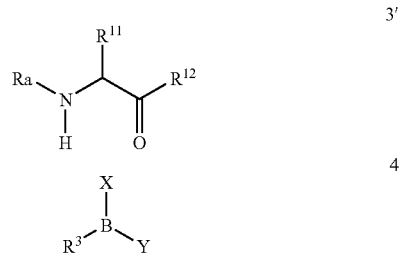

thereby forming the compound represented formula 17'.

7. The method of claim 6, wherein one of $R^1$, $R^2$, $R^3$, $R^4$, $R^9$, $R^{10}$, $R^{11}$, $R^{12}$, Rw, X or Y is connected to a polymeric chain or other solid phase material.

8. The method of claim 6, wherein the compound of formula 17 is formed as a member of a combinatorial library.

9. The method of claim 7, wherein the compound of formula 17 is formed as a member of a combinatorial library.

10. The method of claim 1, wherein Rw is hydrogen.

11. The method of claim 6, wherein Rw is hydrogen.

* * * * *